United States Patent
Karo et al.

(10) Patent No.: US 8,820,531 B2
(45) Date of Patent: Sep. 2, 2014

(54) PAD TRAY FOR ACCOMODATING AN ELECTRODE

(75) Inventors: Hiromichi Karo, Kyoto (JP); Tomoya Ijiri, Kameoka (JP); Yasuo Tsukahara, Nara (JP)

(73) Assignee: Omron Healthcare Co., Ltd, Kyoto (JP)

( * ) Notice: Subject to any disclaimer, the term of this patent is extended or adjusted under 35 U.S.C. 154(b) by 0 days.

(21) Appl. No.: 14/007,768

(22) PCT Filed: Apr. 13, 2012

(86) PCT No.: PCT/JP2012/060124
§ 371 (c)(1),
(2), (4) Date: Sep. 26, 2013

(87) PCT Pub. No.: WO2012/157380
PCT Pub. Date: Nov. 22, 2012

(65) Prior Publication Data
US 2014/0018658 A1    Jan. 16, 2014

(30) Foreign Application Priority Data

May 16, 2011    (JP) .................................. 2011-109651

(51) Int. Cl.
| | | |
|---|---|---|
| *B65D 85/816* | (2006.01) | |
| *A61B 5/0408* | (2006.01) | |
| *H05K 13/00* | (2006.01) | |
| *A61B 5/00* | (2006.01) | |
| *A61B 5/053* | (2006.01) | |
| *A61N 1/04* | (2006.01) | |

(52) U.S. Cl.
CPC ....... *H05K 13/003* (2013.01); *A61B 2562/0209* (2013.01); *A61B 5/04087* (2013.01); *A61B 5/4872* (2013.01); *A61B 2562/046* (2013.01); *A61B 5/0537* (2013.01); *A61N 1/0492* (2013.01); *A61N 1/0496* (2013.01)
USPC .......................................... 206/701; 600/396

(58) Field of Classification Search
CPC . H05K 13/0084; A61N 1/046; A61N 1/0492; A61B 5/0408; A61B 5/04087
USPC ........................... 206/701; 600/396; 607/142
See application file for complete search history.

(56) References Cited

U.S. PATENT DOCUMENTS

| | | | | |
|---|---|---|---|---|
| 4,362,165 | A * | 12/1982 | Carmon et al. | 600/396 |
| 6,142,305 | A * | 11/2000 | Sembach | 206/701 |
| 2010/0121216 | A1* | 5/2010 | Hamaguchi et al. | 600/547 |

FOREIGN PATENT DOCUMENTS

| | | |
|---|---|---|
| JP | A 3-26277 | 2/1991 |
| JP | A 4-244171 | 9/1992 |
| JP | A 4-303415 | 10/1992 |

OTHER PUBLICATIONS

Jul. 3, 2012 Search Report issued in International Patent Application No. PCT/JP2012/060124 (with translation).

* cited by examiner

*Primary Examiner* — Christopher D Koharski
*Assistant Examiner* — Michael Carey
(74) *Attorney, Agent, or Firm* — Oliff PLC

(57) ABSTRACT

A pad tray includes a base portion and a recessed region that is formed in the front side of the base portion and is for accommodating an electrode pad, the recessed region having a bottom region and a sidewall region that extends up from the bottom region and is provided so as to surround the electrode pad.

13 Claims, 27 Drawing Sheets

PAD TRAY FOR ACCOMODATING AN ELECTRODE

CROSS REFERENCE TO RELATED APPLICATIONS

This application is a Continuation of Japanese Application No. 2011-109651, filed May 16, 2011, the entire contents of which is incorporated by reference in its entirety.

TECHNICAL FIELD

This invention relates to pad trays for accommodating electrode pads to be mounted on electrodes that come in contact with a living body.

BACKGROUND ART

With electrodes that come in contact with a living body, a hydrous conductive gel that has conductivity and high flowability (hereinafter, flowable conductive gel (commonly referred to as "gel")) is applied to the surface of the electrodes, with a view to improving adhesiveness to the living body and skin followability. The aim is to improve the accuracy with which electric signals from a living body are measured by reducing contact resistance between the electrodes and the living body.

Note that "gel" usually denotes a (jelly-like) substance consisting of a lyophilic colloidal solution and having elastic force and low flowability. Accordingly, in this specification, a substance indicated as "conductive gel" denotes the usual (jelly-like) substance having elastic force and low flowability, while "flowable conductive gel" denotes a substance that lacks elastic force and is high in flowability.

However, before measurement is performed, the flowable conductive gel needs to be applied to each electrode using a tube. Also, after measurement has been performed, the flowable conductive gel needs to be wiped off the electrode surface and the living body. The task of applying the flowable conductive gel and wiping it off is troublesome for the person carrying out the measurement.

Note that JP 04-244171A (Patent Literature 1), and JP 04-303415A (Patent Literature 2) disclose biomedical electrodes that have a flowable conductive gel provided on the surface of the electrode that comes in contact with a living body.

CITATION LIST

Patent Literature

Patent Literature 1: JP 04-244171A
Patent Literature 2: JP 04-303415A

SUMMARY OF INVENTION

Technical Problem

If electrode pads having a conductive gel are used with electrodes, the work required to perform the task of applying a flowable conductive gel and wiping it off can be reduced. However, a new issue has arisen concerning the handling of electrode pads having a conductive gel.

An object of this invention is to provide a pad tray that facilitates the handling of electrode pads when using electrode pads having a conductive gel.

Solution to Problem

A "conductive gel" in the following description denotes a gel made of a (jelly-like) substance consisting of a lyophilic colloidal solution and having elastic force and low flowability.

A pad tray based on this invention is a pad tray for accommodating an electrode pad that has a conductive gel and a holding face for holding the conductive gel so as to be contactable with an externally provided electrode, and includes a base member that is provided so as to be attachable to and detachable from the electrode, the pad tray having the following configuration.

The pad tray includes a base portion, and a recessed region that is formed in a front side of the base portion and is for accommodating the electrode pad, the recessed region having a bottom region, and a sidewall region that extends up from the bottom region and is provided so as to surround the electrode pad.

In another configuration, the recessed region further includes an abutting portion that, when the electrode pad is accommodated, abuts the holding face and forms a predetermined gap between the holding face and the bottom region.

In another configuration, the recessed region further has a supporting region that is provided so as to project from the sidewall region, and biases the electrode pad toward the bottom region in a state where the electrode pad is accommodated in the recessed region.

In another configuration, the electrode has a cylindrical shape, the electrode pad has a cylindrical shape open at one end, and has, on an inner side thereof, a raised region for engaging an outer peripheral surface of the electrode, and the supporting region is provided in a position that is displaced from the raised region on a circumference when the electrode pad is accommodated in the recessed region.

In another configuration, a force with which the electrode pad is sandwiched by the supporting region and the bottom region is smaller than a force with which the raised region engages the outer peripheral surface of the electrode.

In another configuration, the pad tray further includes a belt material for holding the electrode, the electrode is arranged in a plurality of locations on the belt material at a predetermined interval, and the recessed region is provided at an interval equal to the predetermined interval.

In another configuration, the belt material has a rectangular shape having a short side and a long side, the electrode is arranged, in a direction of the short side, in a plurality of locations on the belt material at a first short-side interval, and the recessed region is provided at an interval equal to the first short-side interval.

In another configuration, the belt material has a rectangular shape having a short side and a long side, the electrode is arranged, in a direction of the long side, at a plurality of locations on the belt material at a first long-side interval, and the recessed region is provided at an interval equal to the first long-side interval.

In another configuration, the belt material has a rectangular shape having a short side and a long side, the electrode is arranged, in a direction of the short side, in a plurality of locations on the belt material at a first short-side interval, the electrode is arranged, in a direction of the long side, at a plurality of locations on the belt material at a first long-side interval, and the recessed region is provided at an interval equal to the first short-side interval in the direction of the short side, and at an interval equal to the first long-side interval in the direction of the long side.

In another configuration, the belt material has a rectangular shape having a short side and a long side, the electrode is arranged on the belt material in order of a first electrode, a second electrode, a third electrode and a fourth electrode in a direction of the long side, the first electrode and the second electrode are arranged at a first long-side interval, the second electrode and the third electrode are arranged at a second long-side interval, and the third electrode and the fourth electrode are arranged at a third long-side interval.

The recessed region has a first recessed region for accommodating the first electrode, a second recessed region for accommodating the second electrode, a third recessed region for accommodating the third electrode, and a fourth recessed region for accommodating the fourth electrode, the first recessed region, the third recessed region, the second recessed region and the fourth recessed region are arranged in stated order on the front side of the base portion in the direction of the long side, an interval between the first recessed region and the second recessed region is provided at the first long-side interval, and an interval between the third recessed region and the fourth recessed region is provided at the third long-side interval.

In another configuration, the pad tray is a tabular resin molded article.

In another configuration, a resin material selected from the group consisting of polyethylene terephthalate, polyethylene, polypropylene, acrylonitrile butadiene styrene and polystyrene is used for the resin molded article.

In another configuration, at least the recessed region of the pad tray is provided so as to enable the electrode pad to be visible from a back side, in a state where the electrode pad is accommodated in the recessed region.

In another configuration, at least the recessed region of the pad tray has translucency.

Advantageous Effects of Invention

A pad tray based on this invention facilitates handling of electrode pads having a conductive gel.

DESCRIPTION OF EMBODIMENTS

Figure 1:
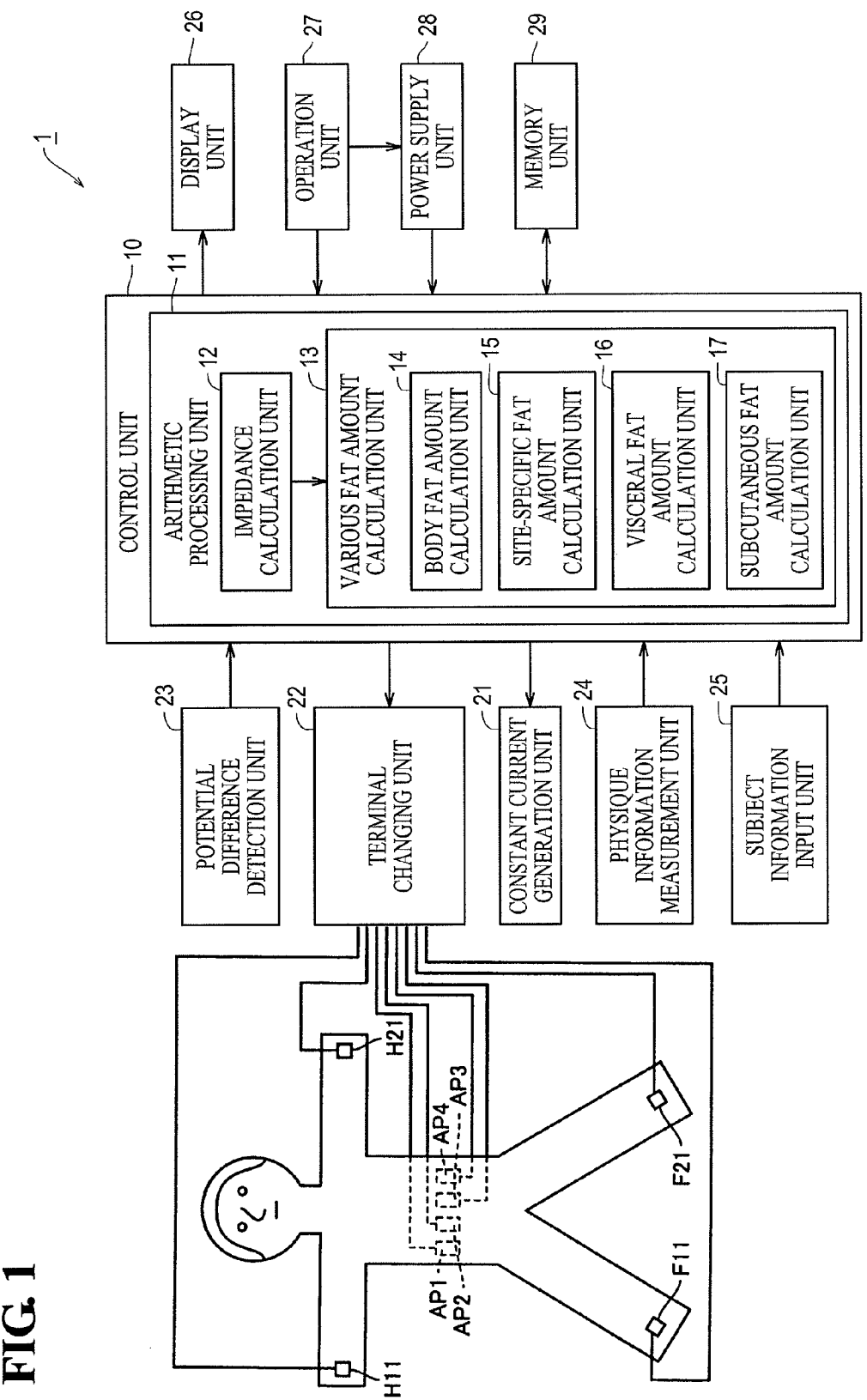
FIG. 1 is a functional block diagram of a body fat measuring device according to an embodiment.

Hereinafter, electrode pads and pad trays for accommodating the electrode pads according to embodiments based on this invention will be described in detail with reference to the diagrams. Note that, in the case where numbers, amounts or the like are referred to in each embodiment described below, the scope of the invention is not necessary limited to those numbers, amounts or the like, unless expressly stated otherwise. Note also that, in the case where multiple embodiments are given hereinafter, appropriately combining the configurations of individual embodiments was intended from the outset, unless expressly stated otherwise. The same reference numerals in the drawings indicate the same or equivalent portions, and redundant description may be omitted.

The embodiments shown below will be described giving an example of a body fat measuring device configured to be able to measure not only the amount of visceral fat but also the total amount of fat in the body and the amount of fat in specific sites on the body (the amount of fat in the upper and lower limbs, the amount of fat in the trunk, the amount of subcutaneous abdominal fat, etc.). That is, the "body fat measuring device" includes a "visceral fat measuring device".

Note that the "abdomen" is the part of the trunk excluding the chest. Also, "sites separate from the abdomen" include the upper limbs consisting of the upper arm, forearm, wrist and fingers, parts of the chest that are a predetermined distance (e.g., approx. 10 cm) or more from the diaphragm, the upper body including the shoulder, neck and head, and the lower limbs consisting of the thigh, lower leg, ankle and toes. Also, the "body axis" is an axis that is approximately perpendicular to the traverse plane of the subject's abdomen. Also, the "front of the abdomen" includes parts of subject's abdomen that are visible when the subject is observed from the front; for example, parts of the subject's abdomen that are visible when the subject is observed from the navel side, along an axis that passes through the subject's navel and backbone and is perpendicular to the subject's body axis. Also, the "back of the abdomen" includes parts of the subject's abdomen that are visible when the subject is observed from behind; for example, parts of subject's abdomen that are visible when the subject is observed from the backbone side, along an axis that passes through the subject's navel and backbone and is perpendicular to the subject's body axis.

Body Fat Measuring Device

FIG. 1 is a functional block diagram of the body fat measuring device according to the present embodiment. First, a configuration of the body fat measuring device will be described, with reference to FIG. 1.

Referring to FIG. 1, a body fat measuring device 1 is mainly provided with a control unit 10, a constant current generation unit 21, a terminal changing unit 22, a potential difference detection unit 23, a physique information measurement unit 24, a subject information input unit 25, a display unit 26, an operation unit 27, a power supply unit 28, a memory unit 29, and a plurality of electrodes. The control unit 10 includes an arithmetic processing unit 11.

The body fat measuring device 1 is provided with abdomen electrode pairs AP1 to AP4 for mounting on the back of the subject's abdomen, upper-limb electrodes H11 and H21 for mounting on the subject's upper limbs, and lower-limb electrodes F11 and F21 for mounting on the subject's lower limbs, as the plurality of electrodes.

The control unit 10 is constituted by a CPU (Central Processor Unit), for example, and performs overall control of the body fat measuring device 1. Specifically, the control unit 10 performs processing such as sending instructions to the various functional blocks mentioned above and performing various types of arithmetic processing based on obtained information. Of these, the various types of arithmetic processing are performed by the arithmetic processing unit 11 provided in the control unit 10.

The abdomen electrode pairs AP1 to AP4 are respectively to be mounted on the surface of the back of the subject's abdomen in the body axis direction. The upper-limb electrodes H11 and H21 favorably are respectively to be mounted on the surface of the right wrist and the surface of the left wrist. The lower-limb electrodes F11 and F21 favorably are respectively to be mounted on the surface of the right ankle and the surface of the left ankle. The abdomen electrode pairs AP1 to AP4, the upper-limb electrodes H11 and H21 and the lower-limb electrodes F11 and F21 are respectively electrically connected to the terminal changing unit 22.

The terminal changing unit 22 is constituted by a plurality of relay circuits, for example. The terminal changing unit 22 electrically connects a specific electrode pair selected from the abovementioned plurality of electrodes to the constant current generation unit 21, and electrically connects a specific electrode pair selected from the abovementioned plurality of electrodes to the potential difference detection unit 23, based on instructions received from the control unit 10.

The electrode pair electrically connected to the constant current generation unit 21 by the terminal changing unit 22 will thereby function as a constant current application electrode pair, and the electrode pair electrically connected to the potential difference detection unit 23 by the terminal changing unit 22 will function as a potential difference detection electrode pair. The electrical connections by the terminal changing unit 22 are variously changed during the measurement operation.

The constant current generation unit 21 generates a constant current based on an instruction received from the control unit 10, and supplies the generated constant current to the terminal changing unit 22. The constant current generation unit 21 supplies a high frequency current (e.g., 50 kHz, 500 µA) that favorably is used in order to measure body composition information, for example. The constant current will thereby be applied to the subject via the electrode pair electrically connected to the constant current generation unit 21 by the terminal changing unit 22, that is, via the constant current application electrode pair.

The potential difference detection unit 23 detects the potential difference between the electrodes of the electrode pair electrically connected to the potential difference detection unit 23 by the terminal changing unit 22, that is, the potential difference between the electrodes of the potential difference detection electrode pair, and outputs the detected potential difference to the control unit 10. The potential difference between the electrodes of the potential difference detection electrode pair in a state where a constant current is applied to the subject will thereby be detected.

The physique information measurement unit 24 and the subject information input unit 25 are units for obtaining subject information that is used in the arithmetic processing performed by the arithmetic processing unit 11 of the control unit 10. Here, subject information denotes information relating to the subject, and includes at least one of information such as age, gender and physique information, for example. Also, physique information denotes information relating to the size of a specific site on the subject's body, and includes, for example, at least one of information such as waist length (abdominal circumference), abdominal width and abdominal thickness, as well as information such as height and weight. The physique information measurement unit 24 is a unit for automatically measuring the subject's physique information, and outputs the measured physique information to the control unit 10. On the other hand, the subject information input unit 25 is a unit for receiving input of subject information, and outputs the inputted subject information to the control unit 10.

Note that although the functional block diagram shown in FIG. 1 illustrates the case where the physique information measurement unit 24 and the subject information input unit 25 are both provided in the body fat measuring device 1, the physique information measurement unit 24 and the subject information input unit 25 need not necessarily be configured in such a manner. Whether or not to provide the physique information measurement unit 24 and/or the subject information input unit 25 is selected as appropriate based on the type of subject information that will be utilized in the arithmetic processing performed by the arithmetic processing unit 11 of the control unit 10. Also, a configuration may be adopted where physique information, out of the subject information, is automatically measured by the physique information measurement unit 24, or where the subject manually inputs physique information into the subject information input unit 25.

The arithmetic processing unit 11 includes an impedance calculation unit 12 and a various fat amount calculation unit 13. The impedance calculation unit 12 calculates various impedances based on the current value of the constant current generated by the constant current generation unit 21 and the potential difference information detected by the potential difference detection unit 23 and received by the control unit 10.

The various fat amount calculation unit 13 computes the amounts of various types of fat based on the impedance information obtained by the impedance calculation unit 12 and the subject information received from the physique information measurement unit 24 and/or the subject information input unit 25. The various fat amount calculation unit 13 includes, for example, at least one of a body fat amount calculation unit 14 that calculates the subject's total amount of body fat, a site-specific fat amount calculation unit 15 that calculates the amount of fat in specific sites on the subject's body, a visceral fat amount calculation unit 16 that calculates the amount of the subject's visceral fat, and a subcutaneous fat amount calculation unit 17 that calculates the amount of subcutaneous fat in the subject's abdomen. Note that the body fat amount calculation unit 14 and the subcutaneous fat amount calculation unit 17 may be configured to be included in the visceral fat amount calculation unit 16.

The display unit 26 displays information on the amounts of various types of fat calculated by the arithmetic processing unit 11. An LCD (Liquid Crystal Display), for example, can be used as the display unit 26. Note that exemplary amounts of fat displayed on the display unit 26 include the subject's total amount of body fat, the amount of fat in specific sites on the subject's body, the amount of visceral fat, and the amount of subcutaneous fat in the abdomen. Here, "fat amount" denotes an index indicating an amount of fat such as fat by weight, fat by area, fat by volume, and the level of fat, for example, and in relation to the visceral fat amount, in particular, indicates not only visceral fat by weight but at least one of visceral fat by area, visceral fat by volume, and the level of visceral fat.

The operation unit 27 is a unit for the subject to input commands to the body fat measuring device 1, and is constituted by keys or the like that can be depressed by the subject, for example.

The power supply unit 28 is a unit for supplying electric power to the control unit 10 and the like, examples of which include an internal power supply such as a battery and an external power supply such as a commercial power supply.

The memory unit 29 is a unit for storing various types of data and programs relating to the body fat measuring device 1, and stores, for example, the abovementioned subject information, the calculated amount of visceral fat, and a body fat measurement program for executing body fat measurement processing discussed later.

Next, an example of arithmetic processing performed by the body fat measuring device 1 according to the present embodiment will be described. Although the body fat measuring device 1 according to the present embodiment is, as mentioned above, capable of measuring the amounts of various types of fat with the various fat amount calculation unit 13, arithmetic processing that is implemented when calculating visceral fat by area as an index showing the amount of visceral fat will be illustrated below.

Referring to FIG. 1, the impedance calculation unit 12 calculates two types of impedance, based on the current value that is generated by the constant current generation unit 21 and the potential difference that is detected by the potential difference detection unit 23. One of the two types of impedance is an impedance reflecting the fat-free mass in the subject's abdomen (hereinafter, this impedance will also be referred to as Zt). The other type of impedance is an impedance reflecting the amount of subcutaneous fat in the subject's abdomen (hereinafter, this impedance will also be referred to as Zs).

The visceral fat amount calculation unit 16 calculates an amount of the subject's visceral fat such as the visceral fat area (unit: cm$^2$), for example, based on the two types of impedance Zt and Zs that are calculated and the subject's physique information (waist length). Specifically, a visceral fat area Sv is calculated by the following equation (1) representing the relationship of the visceral fat area with the two types of impedance Zt and Zs and the subject's waist length, for example.

$$Sv = a \times W^2 - b \times (1/Zt) - c \times W \times Zs - d \qquad (1)$$

(where a, b, c, d: coefficients, W: waist length).

Also, the subcutaneous fat amount calculation unit 17 calculates an amount of the subject's subcutaneous fat, such as the subcutaneous fat area (unit: cm$^2$), for example, based on the calculated impedance Zs and the subject's physique information (waist length). Specifically, the subcutaneous fat area Ss is calculated by the following equation (2) representing the relationship of the subcutaneous fat area with the impedance Zs and the subject's waist length, for example.

$$Ss = e \times W \times Zs + f \quad (2)$$

(where e, f: coefficients, W: waist length).

Also, in the case of computing the subject's total amount of body fat, the body fat amount calculation unit 14 calculates the fat-free mass FFM (unit: kg) based on the calculated impedance Zt and one type of information (e.g., height) included in the subject's physique information. Specifically, the fat-free mass FFM is calculated by the following equation (3) representing the relationship of the fat-free mass with the impedance Zt and the subject's height, for example.

$$FFM = i \times H2/Zt + j \quad (3)$$

(where i, j: coefficients, H: height).

The coefficients in each of the above equations (1), (2) and (3) are determined by a regression equation that is based on MRI (Magnetic Resonance Imaging) measurement results, for example. Also, the coefficients in each of equation (1), (2) and (3) may be determined by age and/or gender.

The body fat amount calculation unit 14 then calculates an amount of the subject's body fat, such as the body fat percentage (%), for example, based on the calculated impedance Zt and at least one type of information (e.g., weight) included in the subject information. Specifically, the body fat percentage is calculated by the following equation (4), based on the fat-free mass FFM and the subject's weight, for example.

$$\text{Body fat percentage} = (Wt - FFM)/Wt \times 100 \quad (4)$$

(where Wt: weight).

Figure 2:
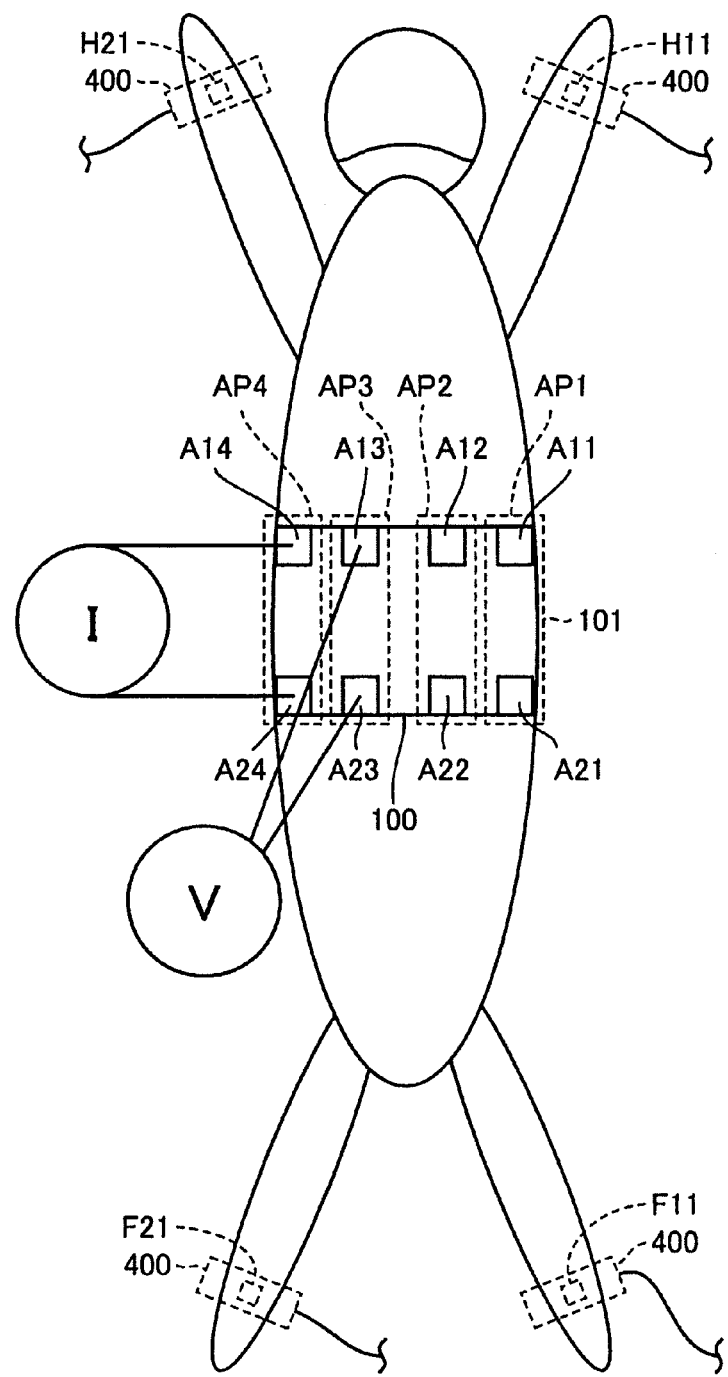
FIG. 2 is a diagram showing an exemplary arrangement of electrodes of the body fat measuring device according to the embodiment (as viewed from the back side).

FIG. 2 is a diagram showing an exemplary arrangement of the electrodes in the body fat measuring device according to the embodiment of the present invention. A state where upper-limb electrodes, lower-limb electrodes and abdomen electrodes are arranged is shown in FIG. 2. FIG. 2 shows an exemplary arrangement of electrodes as viewed from the back side of the subject.

Referring to FIG. 2, the body fat measuring device 1 is provided with an electrode belt 100 and limb clips 400. The electrode belt 100 is formed by integrating the abdomen electrode pairs AP1, AP2, AP3 and AP4 with a belt material 101. The abdomen electrode pair AP1 includes abdomen electrodes A11 and A21. The abdomen electrode pair AP2 includes abdomen electrodes A12 and A22. The abdomen electrode pair AP3 includes abdomen electrodes A13 and A23. The abdomen electrode pair AP4 includes abdomen electrodes A14 and A24.

The abdomen electrode pairs AP1, AP2, AP3 and AP4 are arranged in the body axis direction on the back of the subject's abdomen, and are arranged with intervals therebetween in a direction that is approximately perpendicular to the body axis. For example, the abdomen electrode pair AP2 is arranged at a predetermined distance away from an axis passing through the abdomen electrodes A11 and A21 of the abdomen electrode pair AP1.

The inter-electrode distances of the abdomen electrode pairs AP1, AP2, AP3 and AP4 are approximately equal. For example, the distance between the abdomen electrodes A11 and A21 of the abdomen electrode pair AP1 and the distance between the abdomen electrodes A12 of A22 of the abdomen electrode pair AP2 are approximately equal. Each of the electrodes of the abdomen electrode pairs AP1, AP2, AP3 and AP4 is arranged so as to be aligned with the corresponding electrode in the other electrode pairs in a direction approximately perpendicular the body axis. That is, the abdomen electrodes A11, A12, A13 and A14 are arranged in a row in a direction approximately perpendicular the body axis, and the abdomen electrodes A21, A22, A23 and A24 are arranged in a row in a direction approximately perpendicular the body axis.

Note that abdomen electrode pairs AP1, AP2, AP3 and AP4 may be configured to be arranged at a row in the body axis direction. That is, the abdomen electrode pairs AP2, AP3 and AP4 may be configured to be arranged on an axis passing through the abdomen electrodes AP11 and AP21 of the abdomen electrode pair AP1.

Also, a given abdomen electrode pair may be configured to be arranged in a position sandwiching another abdomen electrode pair. For example, the abdomen electrode pairs AP1 and AP2 may be arranged in a row in the body axis direction, and the pair of abdomen electrodes AP1 may be arranged in positions sandwiching the abdomen electrode pair AP2. Also, the abdomen electrode pairs AP3 and AP4 may be arranged in a row in the body axis direction, and the pair of abdomen electrodes AP3 may be arranged in positions sandwiching the abdomen electrode pair AP4.

The limb clips 400 respectively hold the upper-limb electrodes H11 and H21 and the lower-limb electrodes F11 and F21, and are mounted on the surface of the right wrist, the surface of the left wrist, the surface of the right ankle and the surface of the left ankle.

The constant current generation unit 21 sends current through the electrodes of the electrode pair electrically connected to the constant current generation unit 21 by the terminal changing unit 22 (hereinafter also referred to as the current electrode pair).

The potential difference detection unit 23 then detects the potential difference between the electrodes of the electrode pair electrically connected to the potential difference detection unit 23 by the terminal changing unit 22 (hereinafter also referred to as the voltage electrode pair).

The visceral fat amount calculation unit 16 calculates the amount of the subject's visceral fat based on the potential difference between the electrodes of the voltage electrode pair detected by the potential difference detection unit 23.

Operations of Body Fat Measuring Device

Next, operations at the time of the amount of visceral fat being measured by the body fat measuring device according to the present embodiment will be described.

Figure 3:
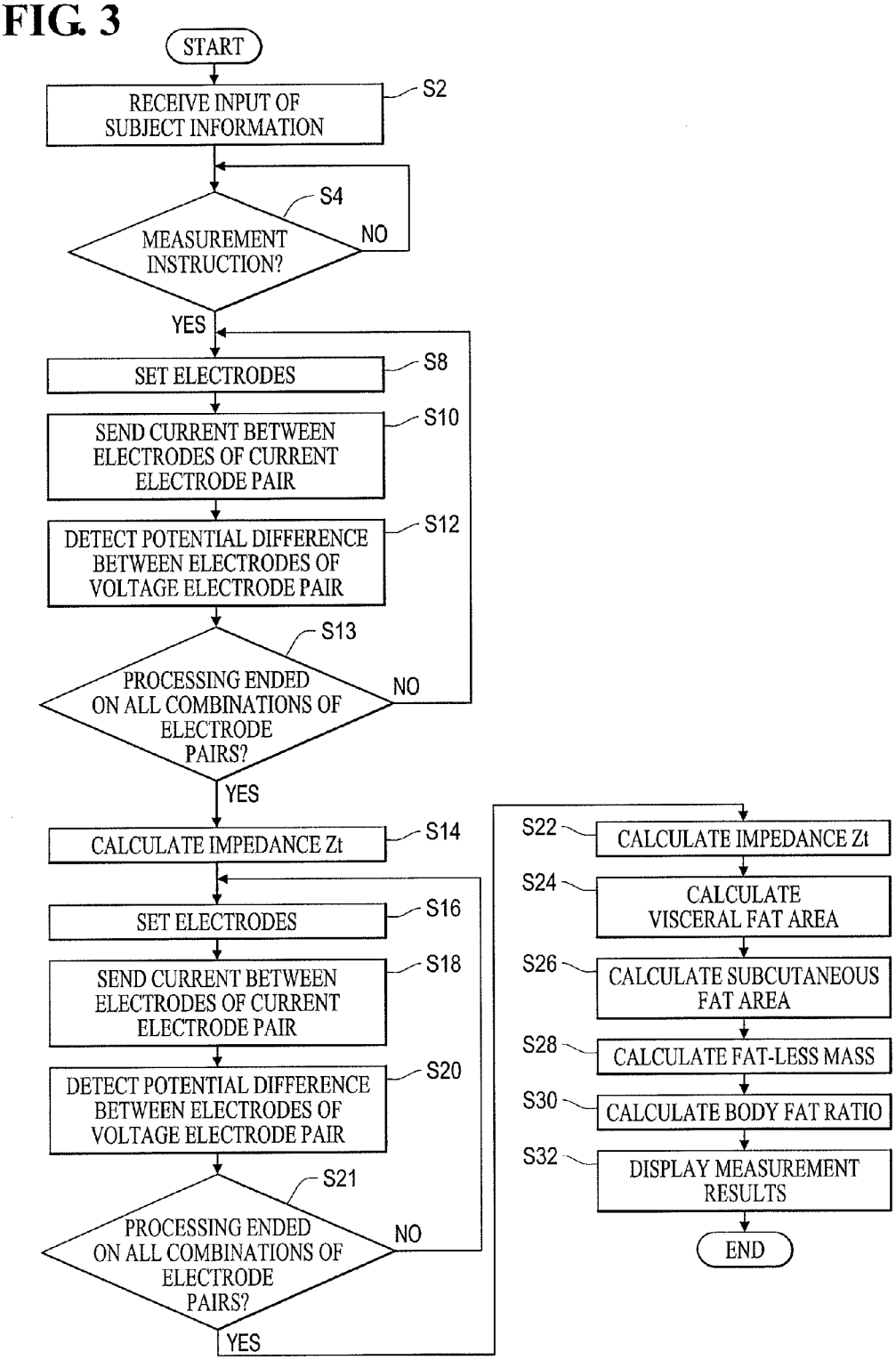
FIG. 3 is a flowchart defining operation procedures at the time of the amount of visceral fat being measured by the body fat measuring device according to the embodiment.

FIG. 3 is a flowchart defining operation procedures at the time of the amount of visceral fat being measured by the body fat measuring device according to the present embodiment. The processing shown in the flowchart of FIG. 3 is stored in advance as a program in the memory unit 29, and the function of visceral fat measurement processing is realized by the control unit 10 reading out and executing this program.

Referring to FIG. 3, the control unit 10 receives input of subject information including physique information (waist length) (step S2). The subject information received here is temporarily saved in the memory unit 29, for example.

Next, the control unit 10 judges whether there is a measurement start instruction (step S4). The control unit 10 waits until there is a measurement start instruction (NO in step S4). The control unit 10, in the case where a measurement start instruction is detected (YES in step S4), configures the electrode settings (step S8).

More specifically, the control unit 10 first performs processing for calculating the impedance Zt. That is, the control unit 10 respectively selects the pair of the upper-limb electrode H11 and the lower-limb electrode F11 and the pair of the upper-limb electrode H21 and the lower-limb electrode F21 as the current electrode pairs, and selects the abdomen electrode pair AP1 as the voltage electrode pair, for example.

The terminal changing unit 22, under the control of the control unit 10, electrically connects the pair of the upper-limb electrode H11 and the lower-limb electrode F11 and the pair of the upper-limb electrode H21 and the lower-limb electrode F21 to the constant current generation unit 21, and electrically connects the abdomen electrode pair AP1 to the potential difference detection unit 23 (step S8). Here, the terminal changing unit 22, under the control of the control unit 10, disconnects the electrical connections of the constant current generation unit 21 and the potential difference detection unit 23 with electrodes that are not selected.

The constant current generation unit 21, under the control of the control unit 10, sends current from the upper limbs toward to the lower limbs. For example, the constant current generation unit 21 sends current from the upper-limb electrode H11 and the upper-limb electrode H21 to the lower-limb electrode F11 and the lower-limb electrode F21 (step S10). In this case, the terminal changing unit 22 desirably is configured to short circuit the upper-limb electrode H11 and the upper-limb electrode H21 and to short circuit the lower-limb electrode F11 and the lower-limb electrode F21. Note that the constant current generation unit 21 and the terminal changing unit 22 may be configured to send current from one of the upper-limb electrodes H11 and H21 to one of the lower-limb electrodes F11 and F21.

In this state, the potential difference detection unit 23, under the control of the control unit 10, detects the potential difference between the abdomen electrodes A11 and A21 of the abdomen electrode pair AP1 (step S12).

The control unit 10 then selects the abdomen electrode pairs AP2, AP3 and AP4 in order as the voltage electrode pair. That is, the terminal changing unit 22, under the control of the control unit 10, electrically connects the abdomen electrode pairs AP2, AP3 and AP4 to the potential difference detection unit 23 in order (step S8). The potential difference detection unit 23, under the control of the control unit 10, then detects the potential difference between the electrodes of each of the abdomen electrode pairs AP2, AP3 and AP4 in order (step S12).

The impedance calculation unit 12, when the detection of potential difference has ended on all combinations of the electrode pairs, that is, here, when detection of the potential difference between the electrodes of each of the abdomen electrode pairs AP1, AP2, AP3 and AP4 has ended (YES at step S13), calculates the impedances Zt1 to Zt4, based on the current values sent by the constant current generation unit 21 and the potential differences detected by the potential difference detection unit 23 (step S14). The values of the impedances Zt1 to Zt4 calculated by the impedance calculation unit 12 are temporarily saved in the memory unit 29, for example.

Next, the control unit 10 performs processing for calculating the impedance Zs. That is, the control unit 10 selects the abdomen electrode pair AP1 as the current electrode pair and selects the abdomen electrode pair AP2 as the voltage electrode pair. The terminal changing unit 22, under the control of the control unit 10, electrically connects the abdomen electrode pair AP1 to the constant current generation unit 21 and electrically connects the abdomen electrode pair AP2 to the potential difference detection unit 23 (step S16). Here, the terminal changing unit 22, under the control of the control unit 10, electrically connects each of the abdomen electrode pairs to the potential difference detection unit 23 selectively, and disconnects the electrical connection of the constant current generation unit 21 and the potential difference detection unit 23 with the unselected abdomen electrode pairs, upper-limb electrodes and lower-limb electrodes.

The constant current generation unit 21, under the control of the control unit 10, sends current through the abdomen electrodes A11 and A21 of the abdomen electrode pair AP1 (step S18).

In this state, the potential difference detection unit 23, under the control of the control unit 10, detects the potential difference between the abdomen electrodes A12 and A22 of the abdomen electrode pair AP2 (step S20).

The control unit 10 selects the abdomen electrode pairs AP3 and AP4 in order as the voltage electrode pair. That is, the terminal changing unit 22, under the control of the control unit 10, electrically connects the abdomen electrode pairs AP3 and AP4 to the potential difference detection unit 23 in order (step S16). The potential difference detection unit 23, under the control of the control unit 10, detects the potential difference between the electrodes of each of the abdomen electrode pairs AP3 and AP4 in order (step S20).

Next, the control unit 10 selects the abdomen electrode pair AP2 as the current electrode pair and selects the abdomen electrode pair AP1 as the voltage electrode pair. That is, the terminal changing unit 22, under the control of the control unit 10, electrically connects the abdomen electrode pair AP2 to the constant current generation unit 21 and electrically connects the abdomen electrode pair AP1 to the potential difference detection unit 23 (step S16).

The constant current generation unit 21, under the control of the control unit 10, sends current through the abdomen electrodes A12 and A22 of the abdomen electrode pair AP2 (step S18).

In this state, the potential difference detection unit 23, under the control of the control unit 10, detects the potential difference between the abdomen electrodes A11 and A21 of the abdomen electrode pair AP1 (step S20).

The control unit 10 selects the abdomen electrode pairs AP3 and AP4 as the voltage electrode pair in order. That is, the terminal changing unit 22, under the control of the control unit 10, electrically connects the abdomen electrode pairs AP3 and AP4 to the potential difference detection unit 23 in order (step S16). The potential difference detection unit 23, under the control of the control unit 10, detects the potential difference between the electrodes of each of the abdomen electrode pairs AP3 and AP4 in order (step S20).

Similarly, the control unit 10 selects the abdomen electrode pairs AP3 and AP4 as the current electrode pair in order, and for each of the abdomen electrode pairs AP3 and AP4, selects the abdomen electrode pairs that are not the current electrode pair, among the abdomen electrode pairs AP1 to AP4, as the voltage electrode pair in order, and respectively detects the potential difference between the electrodes of the voltage electrode pairs (steps S16 to S20).

The impedance calculation unit 12, when the application of current and the detection of potential difference has ended on all combinations of the electrode pairs (YES at step S21), calculates the impedances Zs1 to Zs12, based on the current values sent by the constant current generation unit 21 and the potential differences detected by the potential difference detection unit 23 (step S22). The values of the impedances Zs1 to Zs12 calculated by the impedance calculation unit 12 are temporarily saved in the memory unit 29, for example.

Next, the visceral fat amount calculation unit 16 calculates the visceral fat area Sv based on the physique information (waist length) received by the control unit 10 at step S2, the impedances Zt1 to Zt4 and the impedances Zs1 to Zs12 (step S24). The visceral fat area Sv is calculated by the abovementioned equation (1). Note that, in the case where the body fat measuring device 1 is provided with four abdomen electrode pairs AP1 to AP4, as in the present embodiment, the average value of the four impedances Zt1 to Zt4 is substituted for the impedance Zt in equation (1) and the average value of the twelve impedances Zs1 to Zs12 is substituted for the impedance Zs in equation (1), for example.

Also, the subcutaneous fat amount calculation unit 17 calculates the subcutaneous fat area Ss based on the physique information (waist length) received by the control unit 10 at step S2 and the impedances Zs1 to Zs12 (step S26). The subcutaneous fat area Ss is calculated by the abovementioned equation (2). Note that in the case where the body fat measuring device 1 is provided with four abdomen electrode pairs AP1 to AP4, as in the present embodiment, the average value of the twelve impedances Zs1 to Zs12 is substituted for the impedance Zs in equation (2), for example.

Also, the body fat amount calculation unit 14 calculates the fat-free mass FFM, based on the subject information (e.g., height) input at step S2 and the impedances Zt1 to Zt4 (step S28). The fat-free mass FFM is calculated by the abovementioned equation (3). Note that, in the case where the body fat measuring device 1 is provided with four abdomen electrode pairs AP1 to AP4, as in the present embodiment, the average value of the four impedances Zt1 to Zt4 is substituted for the impedance Zt in equation (3), for example.

Also, the body fat amount calculation unit 14 calculates the body fat percentage, based on the subject information (weight) input at step S2 and the fat-free mass FFM calculated at step S28 (step S30). The body fat percentage is calculated by the abovementioned equation (4).

The display unit 26, under the control of the control unit 10, then displays the measurement results (step S32).

The body fat measuring device 1 therewith ends the body fat measurement processing. Note that a typical value for each of the impedances Zt1 to Zt4 is approximately about 5Ω. Also, a typical value for each of the impedances Zs1 to Zs12 is approximately about 80 Ω.

Electrode Belt 100/Abdomen Electrode 200

Figure 4:
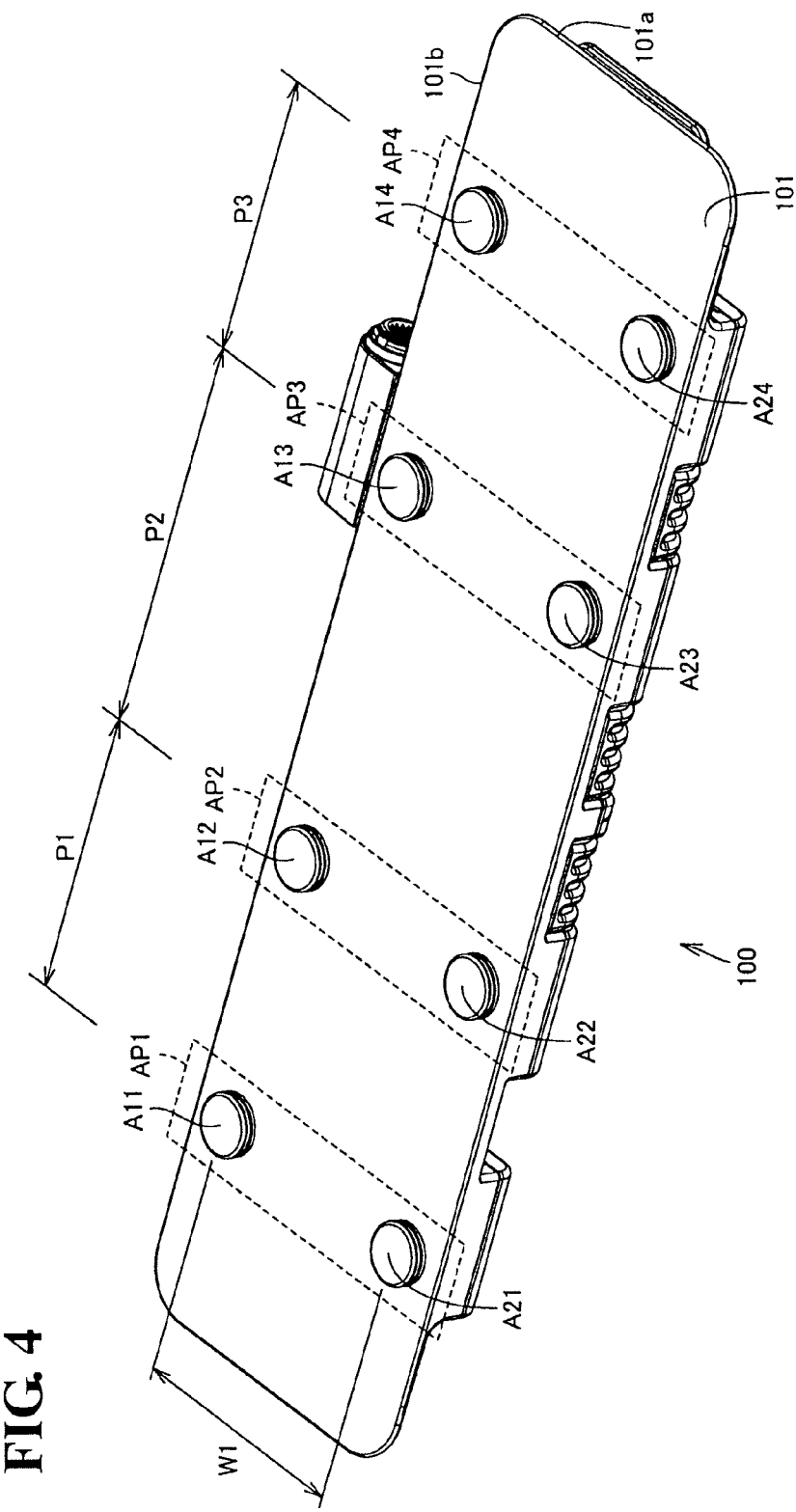
FIG. 4 is a perspective view showing the structure of an electrode belt that is used in the body fat measuring device according to the embodiment.
Figure 5:
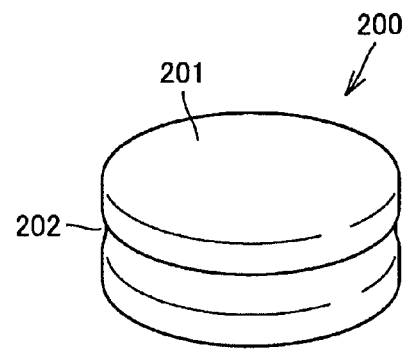
FIG. 5 is a perspective view showing the structure of an abdomen electrode that is provided in the electrode belt used in the body fat measuring device according to the embodiment.

Next, the electrode belt 100 will be described with reference to FIGS. 4 and 5. Note that FIG. 4 is a perspective view showing the structure of an electrode belt that is used in the body fat measuring device, and FIG. 5 is a perspective view showing the structure of an abdomen electrode that is provided in the electrode belt used in the body fat measuring device.

This electrode belt 100 is formed by integrating the abdomen electrode pairs AP1, AP2, AP3 and AP4 with the belt material 101. An elastomeric material is used for the belt material 101, and an accordion-like structure is adopted for part thereof to facilitate wrapping around the subject's abdomen.

The abdomen electrode pair AP1 includes the abdomen electrodes A11 and A21, and the abdomen electrodes A11 and A21 are arranged so as to be separated by a predetermined gap in the body axis direction. Similarly, the abdomen electrode pair AP2 includes the abdomen electrodes A12 and A22, and the abdomen electrodes A12 and A22 are arranged so as to be separated by a predetermined gap in the body axis direction. Similarly, the abdomen electrode pair AP3 includes the abdomen electrodes A13 and A23, and the abdomen electrodes A13 and A23 are arranged so as to be separated by a predetermined gap in the body axis direction. Similarly, the abdomen electrode pair AP4 includes the abdomen electrodes A14 and A24, and the abdomen electrodes A14 and A24 are arranged so as to be separated by a predetermined gap in the body axis direction.

In the present embodiment, the belt material 101 is a rectangular shape having a short side 101a and a long side 101b. The four abdomen electrodes A11, A12, A13 and A14 are arranged on the belt material 101 in the direction of the long side 101b. A first long-side interval between the abdomen electrode A11 and the abdomen electrode A12 is P1, a second long-side interval between the abdomen electrode A12 and the abdomen electrode A13 is P2, and a third long-side interval between the abdomen electrode A13 and the abdomen electrode A14 is P3. Note that, in the present embodiment, P1=P3 and P2>P1. Also, the long-side interval between electrodes denotes the distance between the centers of the electrodes in the direction of the long side 101b.

The four abdomen electrodes A21, A22, A23 and A24 are also arranged in the direction of the long side 101b on the belt material 101, similarly to the abovementioned abdomen electrodes A11, A12, A13 and A14.

Also, the abdomen electrode A11 and the abdomen electrode A21 are arranged in the direction of the short side 101a of the belt material 101. A first short-side interval between the abdomen electrode A11 and the abdomen electrode A21 is W1. Note that the short-side interval between electrodes denotes the distance between the centers of the electrodes in the direction of the short side 101a. The abdomen electrodes A12 to A14 and the abdomen electrodes A22 to A24 are also respectively provided at the first short-side interval W1.

Referring to FIG. 5, the structure of an abdomen electrode 200 that is used for the abdomen electrodes A11, A21, A12, A22, A13, A23, A14 and A24 is shown. The abdomen electrode 200 has a cylindrical shape, with a diameter of approximately about 23 mm and a stack height from the belt material 101 of approximately about 6 mm. The abdomen electrode 200 has a metal cylindrical electrode portion 201, and an annular recessed groove portion 202 is provided around a middle portion of this cylindrical electrode portion 201.

Abdomen Electrode Pad 300

Figure 6:
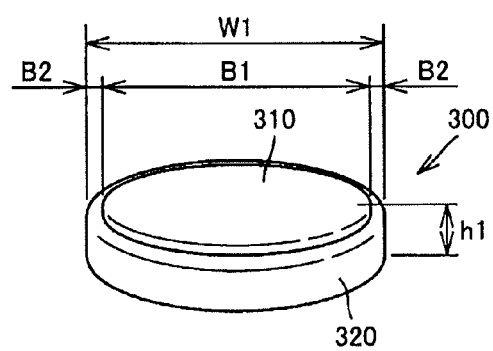
FIG. 6 is a perspective view showing the structure of an abdomen electrode pad according to the embodiment.
Figure 7:
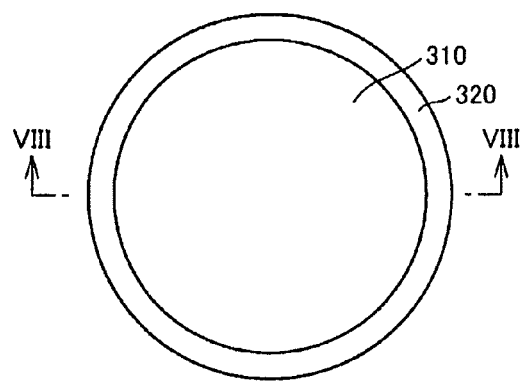
FIG. 7 is a plan view showing the structure of the abdomen electrode pad according to the embodiment.

Next, an abdomen electrode pad 300 that is provided so as to be attachable to and detachable from the abdomen electrode 200 will be described, with reference to FIGS. 6 and 7. Note that FIG. 6 is a perspective view showing the structure of the abdomen electrode pad 300, and FIG. 7 is a plan view showing the structure of the abdomen electrode pad 300. Note also that the gel that is used in the following description denotes a gel made of a (jelly-like) substance consisting of a lyophilic colloidal solution and having elastic force and low flowability.

This abdomen electrode pad 300 is provided with a circular conductive gel 310 and a cylindrical base member 320 that is open at one end, holds the conductive gel 310 so as to be electrically contactable with the abdomen electrode 200, and is provided so as to be attachable to and detachable from the abdomen electrode 200. A material such as a polypropylene-based resin material or ABS resin is used for the base member 320. A material such as an acrylic-based polymer gel or a urethane-based gel is used for the conductive gel 310.

This abdomen electrode pad 300 has an outer diameter (W1) of approximately φ26 mm and a height (h1) including the conductive gel 310 of approximately 7 mm. Also, on the surface portion of the abdomen electrode pad 300, the conductive gel 310 is held by the base member 320 so that the edge (region shown by B2) of the base member 320 is exposed.

In FIG. 6, the region on which the conductive gel 310 is provided (region shown by B1) has a diameter of approximately 22 mm, and the length of the exposed edge portion (region shown by B2) is approximately 2 mm. This enables the abdomen electrode pad 300 to be gripped without the fingertips coming in contact with the conductive gel 310.

Attachment/Detachment of Abdomen Electrode Pad 300 with Respect to Abdomen Electrode 200

Next, attachment/detachment of the abdomen electrode pad 300 with respect to the abdomen electrode 200 will be described, with reference to FIGS. 8 to 10. Note that FIG. 8 is a cross-sectional view along line VIII-VIII of FIG. 7, and FIGS. 9 and 10 are first and second schematic diagrams showing attachment of the abdomen electrode pad 300 to the abdomen electrode.

Figure 8:
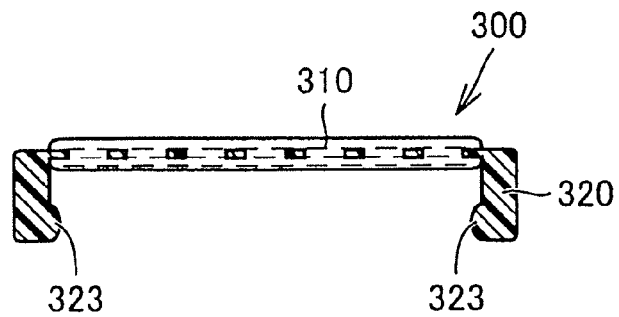
FIG. 8 is a cross-sectional view along line VIII-VIII of FIG. 7.

As shown in FIG. 8, a raised region 323 that projects radially inward is provided on the open end side of the cylindrical base member 320. This raised region 323 may be provided in a continuous annular shape or may be provided discontinuously in a plurality of locations.

Figure 9:
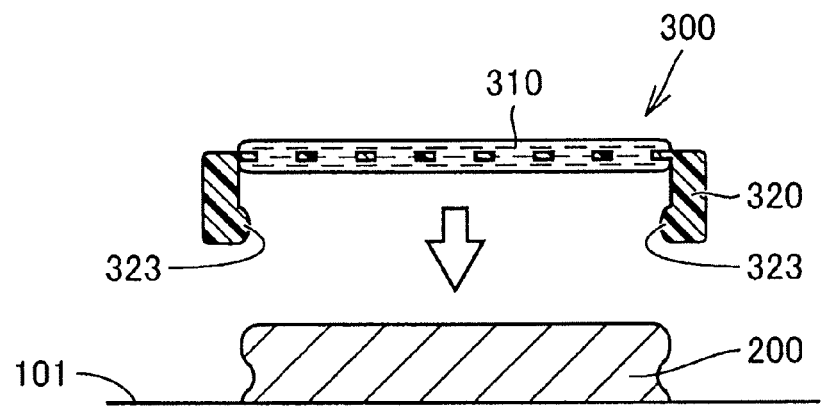
FIG. 9 is a first schematic diagram showing attachment of the abdomen electrode pad according to the embodiment to the abdomen electrode.
Figure 10:
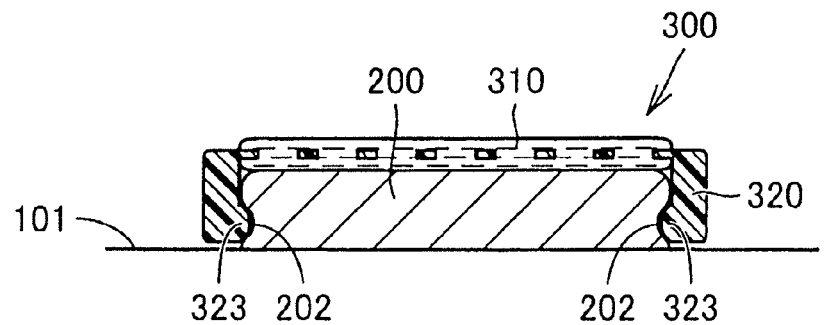
FIG. 10 is a second schematic diagram showing attachment of the abdomen electrode pad according to the embodiment to the abdomen electrode.

By mounting the abdomen electrode pad 300 on the abdomen electrode 200 from above, as shown in FIG. 9, the raised region 323 of the base member 320 elastically deforms so as to be temporarily spread outward, and thereafter the raised region 323 engages the recessed groove portion 202 of the abdomen electrode 200, as shown in FIG. 10. The abdomen electrode pad 300 is thereby fixed to the abdomen electrode 200. At this time, the bottom side of the conductive gel 310 provided on the abdomen electrode pad 300 contacts the top portion of the abdomen electrode 200 in an electrically conductive manner. When removing the abdomen electrode pad 300 from the abdomen electrode 200, the base member 320 is held and lifted up with the fingers.

Detailed Structure of Base Member 320

Figure 11:
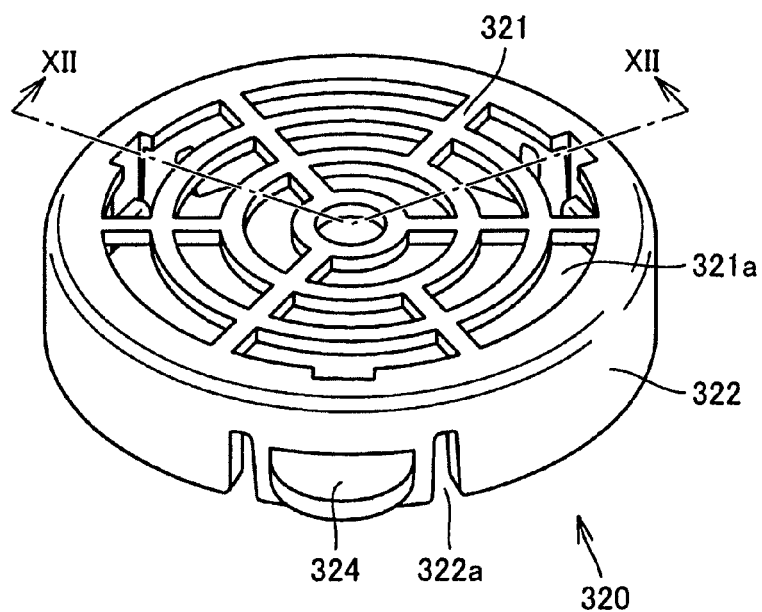
FIG. 11 is a first perspective view showing the structure of a base member of the abdomen electrode pad according to the embodiment as viewed from the front side.
Figure 13:
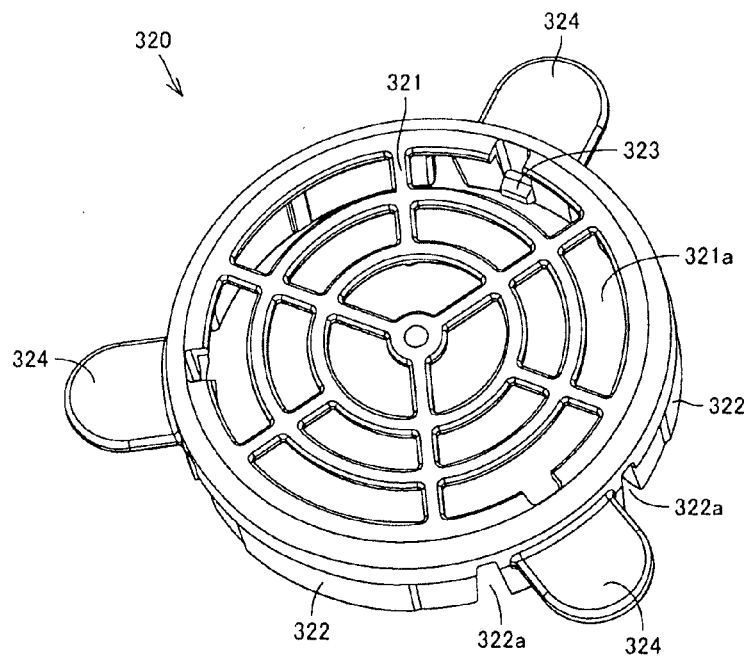
FIG. 13 is a second perspective view showing the structure of the base member of the abdomen electrode pad according to the embodiment as viewed from the front side.
Figure 14:
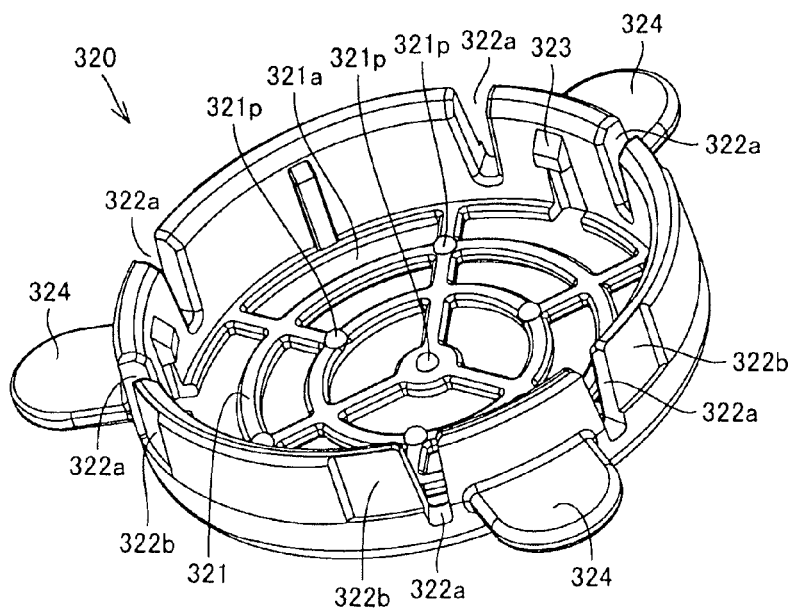
FIG. 14 is a perspective view showing the structure of the base member of the abdomen electrode pad according to the embodiment as viewed from the back side.

Next, the structure of the base member 320 will be described in detail, with reference to FIGS. 11 to 14. Note that FIG. 11 is a first perspective view showing the structure of the base member 320 from the front side, FIG. 12 is a cross-sectional view along line XII-XII of FIG. 11, FIG. 13 is a second perspective view showing the structure of the base member 320 from the front side, and FIG. 14 is a perspective view showing the structure of the base member 320 from the back side.

The base member 320 has a cylindrical body 322 that is open at one end, with a material such as a polypropylene-based resin material or ABS resin being used. The other end of the cylindrical body 322 where the conductive gel 310 is held has a net-like holding face 321 in which a plurality of openings 321a are provided.

The openings 321a formed in the holding face 321 have an opening configuration consisting of a plurality of circular arcs provided in concentric circles. The openings 321a have a radial width of approximately 2 mm, and the holding face 321 that is located between the openings 321a has a width of approximately 1 mm. Utilizing the openings 321a thus formed, the conductive gel 310 is applied to the front side and the back side of the holding face 321, and the conductive gel 310 is held on the holding face 321 so as to be integrally formed with the base member 320.

Figure 12:
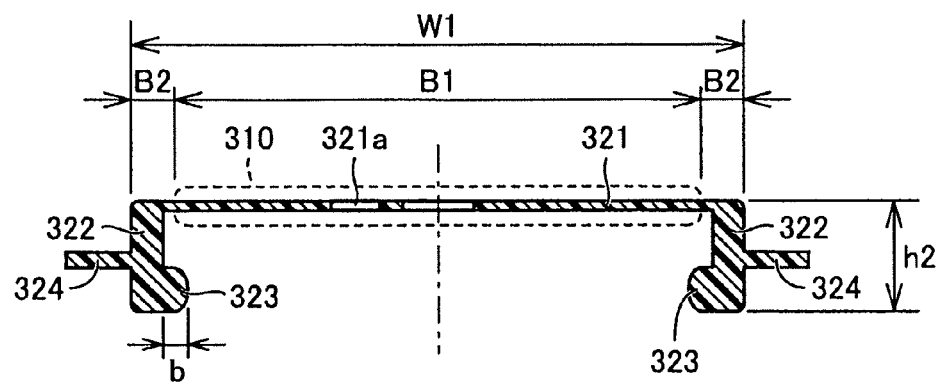
FIG. 12 is a cross-sectional view along line XII-XII of FIG. 11.

Note that the total area of the openings 321a in the region in which the conductive gel 310 is provided (region shown by B1 in FIG. 12) favorably is not less than 50% of the total area of the region in which the conductive gel 310 is provided (region shown by B1 in FIG. 12). The release of air bubbles through the openings is thereby facilitated when applying the conductive gel 310 to the holding face 321 of the base member 320, enabling the entrapment of air bubbles in the conductive gel 310 to be suppressed. As a result, flattening out of the conductive gel 310 over time in portions where there are air bubbles is prevented, and the measurement accuracy of the visceral fat measuring device can be stabilized.

The raised region 323 projecting radially inward is provided in three locations at the open end side of the cylindrical body 322. These raised regions 323 have a projection length (b) of approximately 0.5 mm. Also, the base member 320 has a diameter (W1) of approximately φ26 mm, as mentioned above and a height (h2) of approximately 2 mm.

Also, a slit 322a is provided in a total of six locations in the outer peripheral surface of the cylindrical body 322 in the regions where the raised regions 323 are provided, and a finger tab 324 that juts radially outward is provided in three locations in the regions sandwiched by these slits 322a. Also, the raised regions 323 mentioned above are provided on the inner peripheral surface of the cylindrical body 322 where the finger tabs 324 are provided. When removing the abdomen electrode pad 300 from the abdomen electrode 200, the raised regions 323 move outward as a result of the regions sandwiched by the slits 322a being elastically deformed using these finger tabs 324, thereby enabling the abdomen electrode pad 300 to be easily removed from the abdomen electrode 200. Note that the number of raised regions 323 and the finger tabs 324 is not limited to three, and one, two or four or more can be provided.

Also, a plurality of protrusions 321p are provided on the back side of the holding face 321. By providing the protrusions 321p on the back side of the holding face 321, movement of the holding face 321 toward the abdomen electrode 200 after mounting the abdomen electrode pad 300 on the abdomen electrode 200 is suppressed, even when the abdomen electrode pad 300 is pushed down toward the abdomen electrode 200, as a result of the protrusions 321p abutting against the surface of the abdomen electrode 200. As a result, it is possible to prevent the conductive gel 310 from being pushed out of the holding face 321, and to stop the conductive gel 310 from collapsing.

Detailed Structure of Pad Tray 1000

Figure 16:
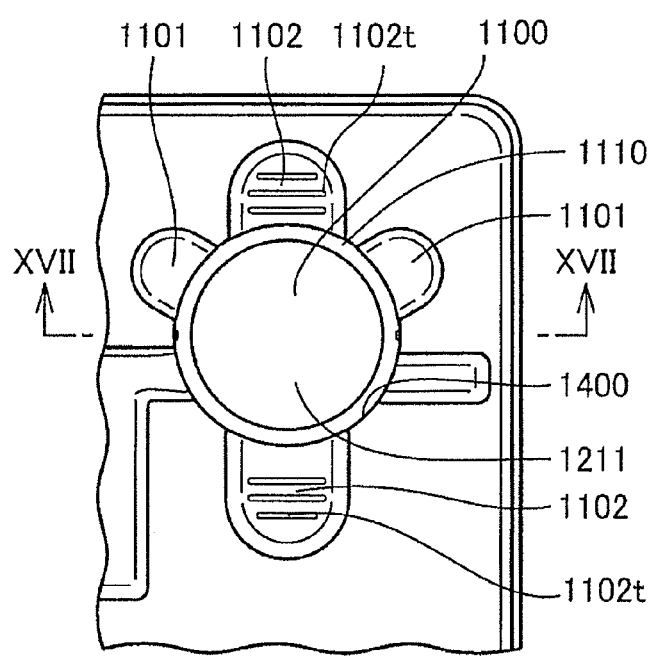
FIG. 16 is a partial enlarged plan view of a recessed region for accommodating an abdomen electrode pad according to the embodiment.
Figure 17:
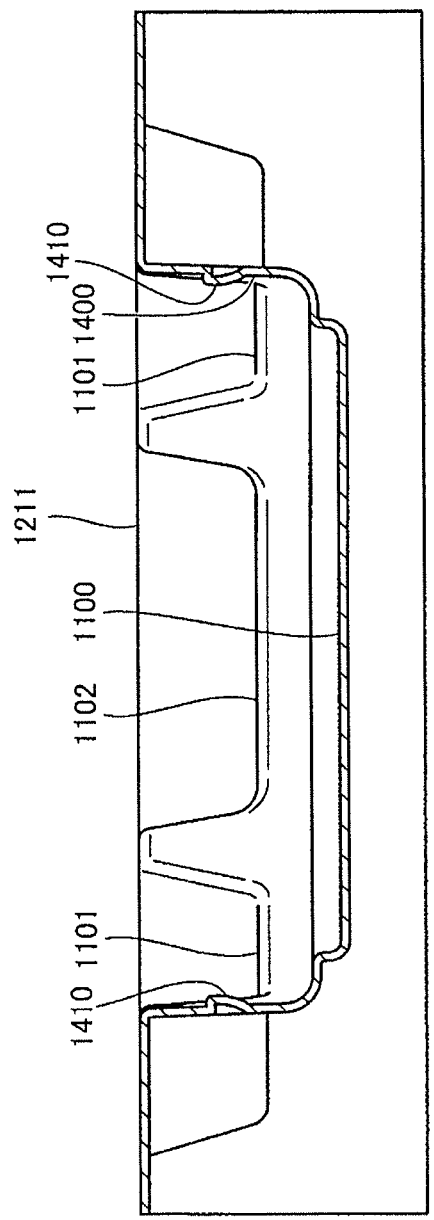
FIG. 17 is a cross-sectional view along line XVII-XVII of FIG. 16.
Figure 18:
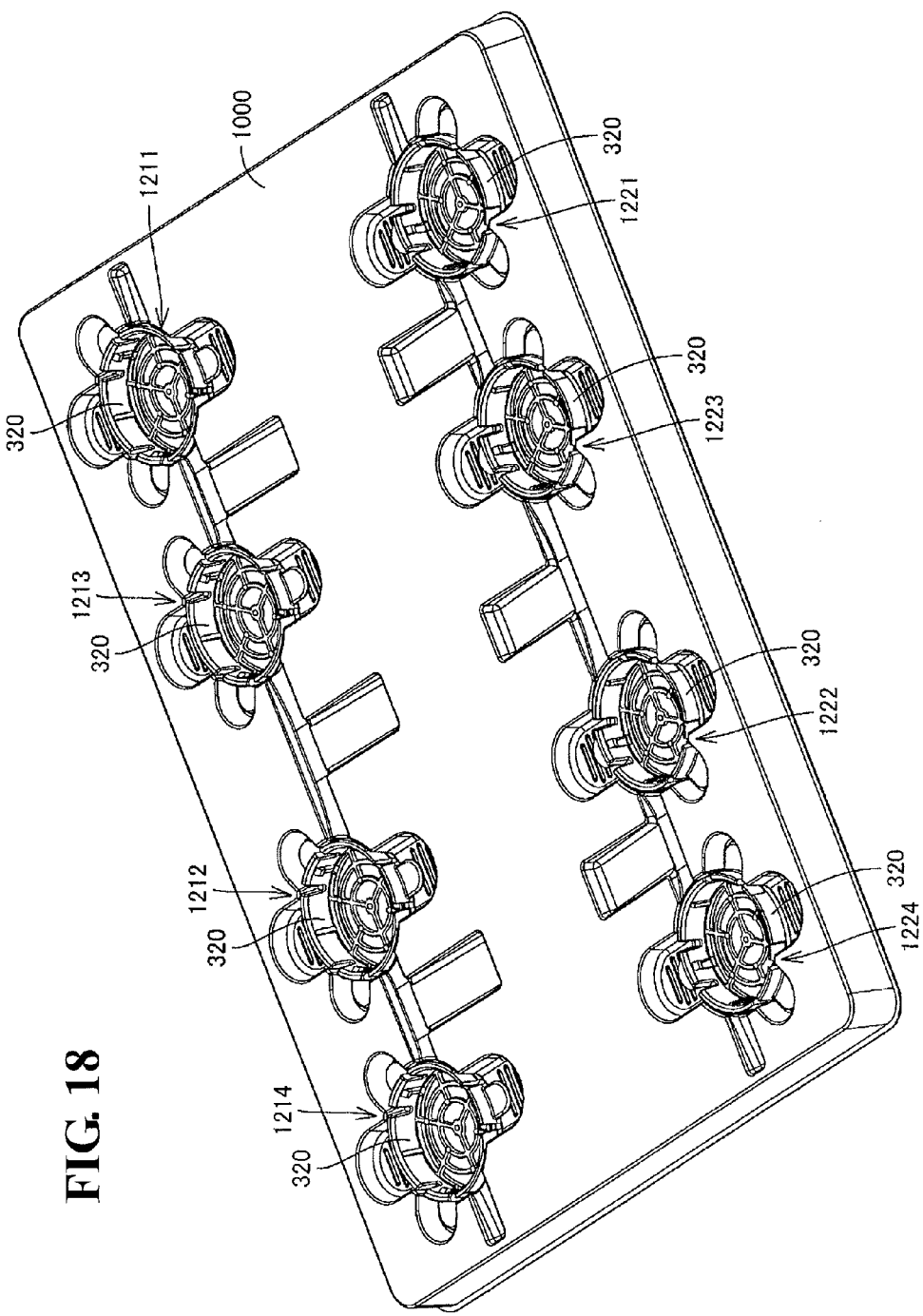
FIG. 18 is a perspective view of a state where abdomen electrode pads are accommodated in the pad tray for accommodating abdomen electrode pads according to the embodiment.
Figure 19:
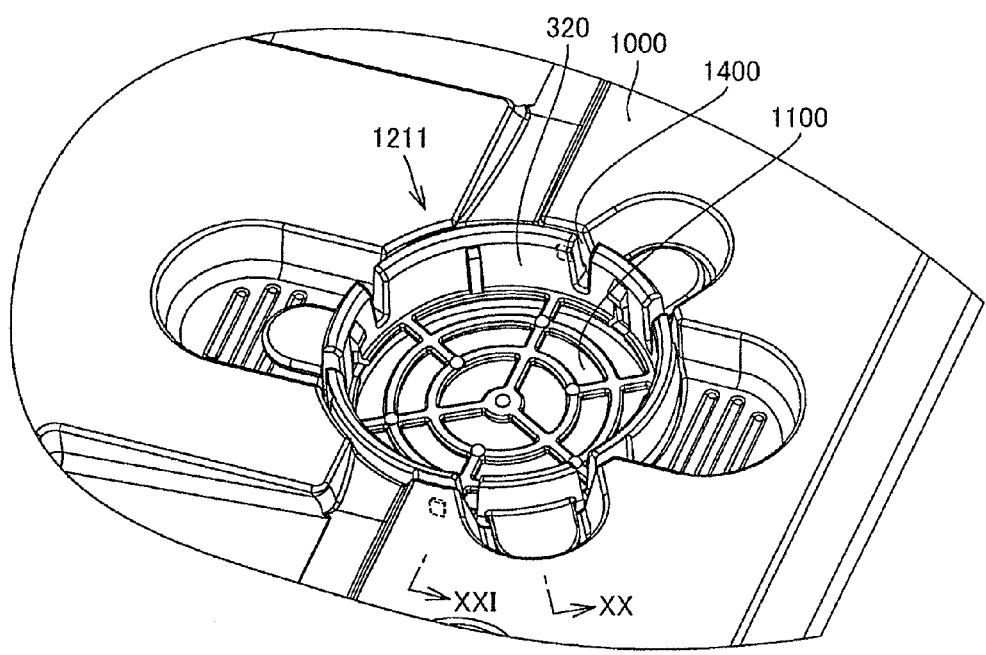
FIG. 19 is a partial enlarged perspective view of a state where an abdomen electrode pad is accommodated in the pad tray for accommodating abdomen electrode pads according to the embodiment.
Figure 20:
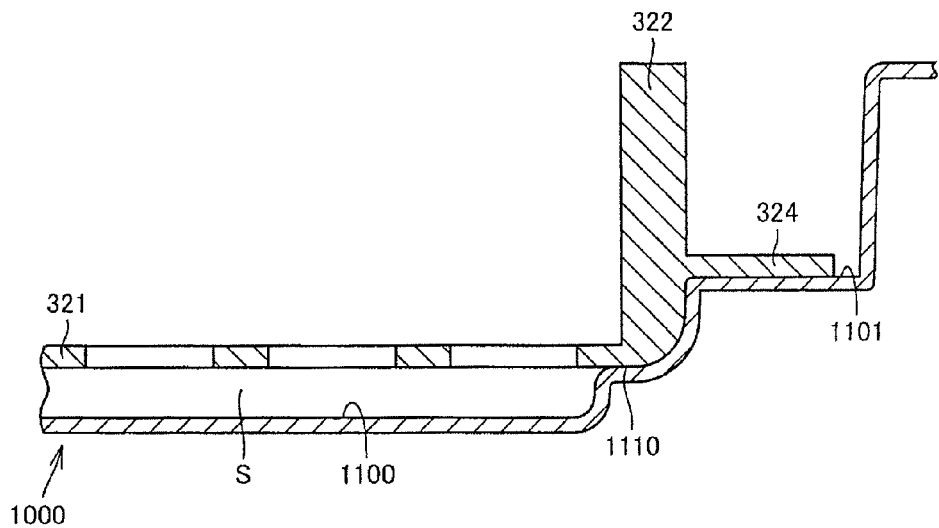
FIG. 20 is a cross-sectional view along line XX of FIG. 19.
Figure 21:
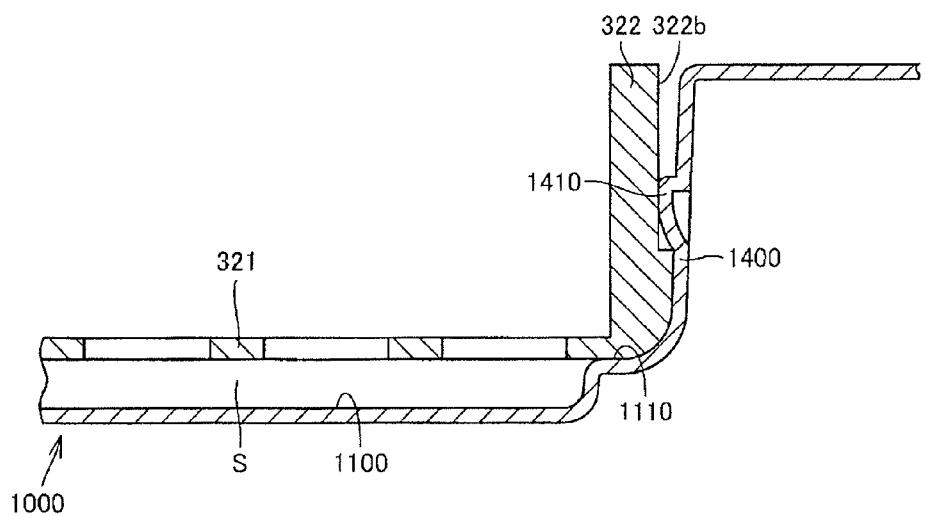
FIG. 21 is a cross-sectional view along line XXI of FIG. 19.

Next, the structure of a pad tray 1000 for accommodating abdomen electrode pads 300 having the above configuration will be described in detail, with reference to FIGS. 15 to 21. Note that FIG. 15 is a perspective view of the pad tray 1000 for accommodating the abdomen electrode pad 300, FIG. 16 is a partial enlarged plan view of a recessed region 1211 for accommodating the abdomen electrode pad 300, FIG. 17 is a cross-sectional view along line XVII-XVII of FIG. 16, FIG. 18 is a perspective view of a state where the abdomen electrode pad 300 is accommodated in the pad tray 1000, FIG. 19 is partial enlarged perspective view of a state where the abdomen electrode pad 300 is accommodated in the pad tray 1000, FIG. 20 is a cross-sectional view along line XX of FIG. 19, and FIG. 21 is a cross-sectional view along line XXI of FIG. 19.

Figure 15:
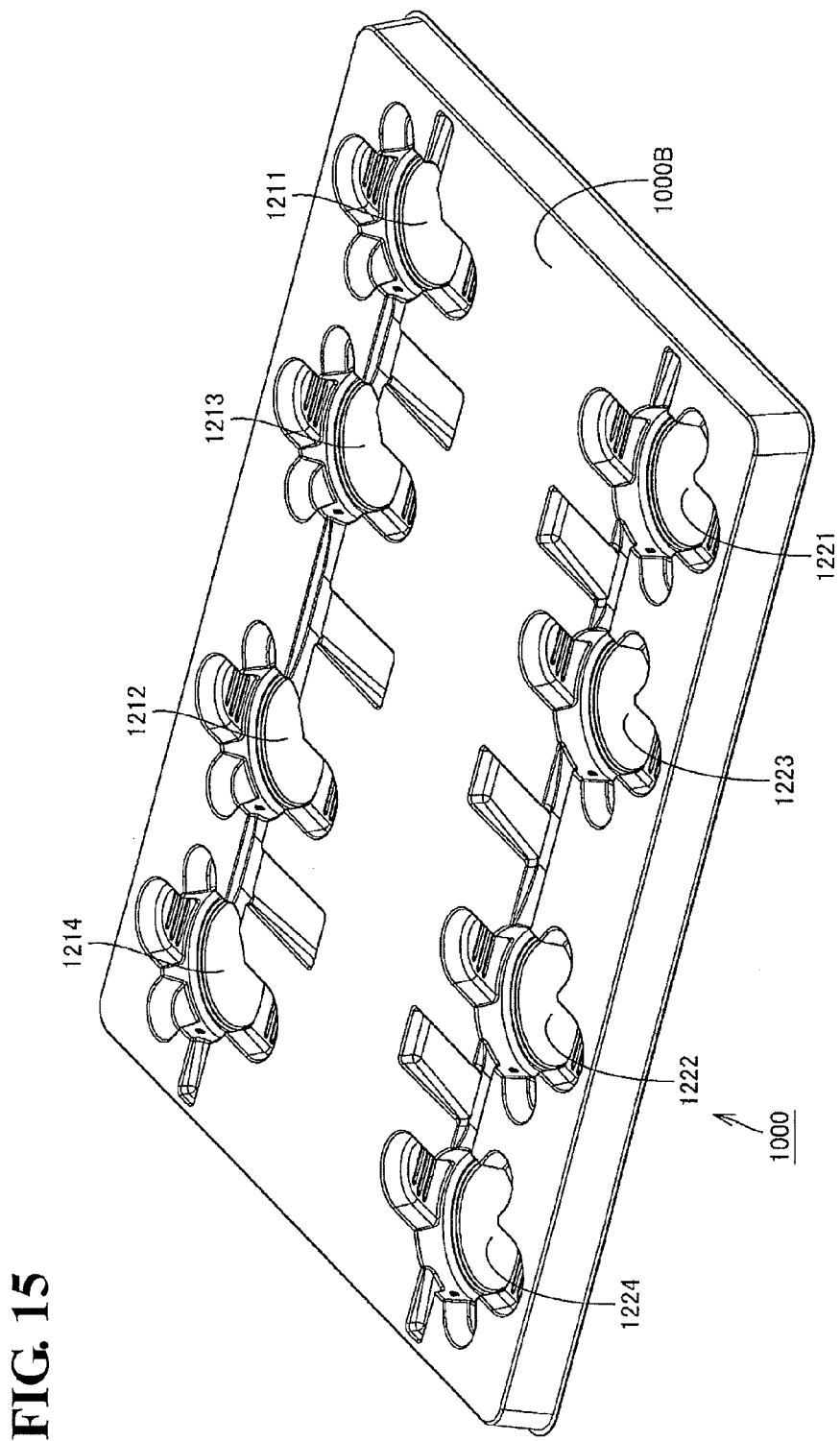
FIG. 15 is a perspective view of a pad tray for accommodating abdomen electrode pads according to the embodiment.

Referring to FIG. 15, the pad tray 1000 according to the configuration of the present embodiment has a base portion 1000B having a rectangular shape, and eight recessed regions 1211, 1212, 1213, 1214, 1221, 1222, 1223 and 1224 formed in the front side of this base portion 1000B that are for accommodating abdomen electrode pads 300 having the abovementioned configuration.

The pad tray 1000 according to the present embodiment is provided with eight recessed regions 1211 to 1214 and 1221 to 1224 that correspond in number to the abdomen electrodes A11 to A14 and A21 to A24 that are adopted in the electrode belt 100 used in the body fat measuring device 1 according to the present embodiment. Accordingly, the number of recessed regions is not limited to eight, and is appropriately decided as needed.

In the present embodiment, a tabular resin molded article is used for the base portion 1000B. As for specific materials, a resin material selected from the group consisting of polyethylene terephthalate (PET), polyethylene (PE), polypropylene (PP), acrylonitrile butadiene styrene (ABS) and polystyrene (PS) is used. In the present embodiment, PET is used.

In the present embodiment, at least the recessed regions 1211 to 1214 and the recessed regions 1221 to 1224 of the pad tray 1000 favorably have translucency, so as to enable visual confirmation of the abdomen electrode pads 300 from the back side, in a state where abdomen electrode pads 300 are accommodated in the recessed regions 1211 to 1214 and the recessed regions 1221 to 1224. Note that, in the present embodiment, the entire pad tray 1000 has translucency.

The shape of the recessed regions 1211 to 1214 and the recessed regions 1221 to 1224 will be described, with reference to FIGS. 16 and 17. In the present embodiment, the shape of the recessed region 1211 will be described, given that the recessed regions 1211 to 1214 and the recessed regions 1221 to 1224 all have the same shape.

The recessed region 1211 has a circular bottom region 1100 and a sidewall region 1400 that extends up from the perimeter of the bottom region 1100 and encloses the abdomen electrode pad 300. Also, a first shallow region 1101 and a second shallow region 1102 that are shallower in depth than the sidewall region 1400 and are for accommodating the finger tabs 324 provided on the abdomen electrode pad 300 are provided.

The first shallow region 1101 is provided in two locations, so as to be able to accommodate two of the three finger tabs 324 that are provided at a pitch of 120 degrees on the abdomen electrode pad 300. The first shallow region 1101 is provided shallower in depth than the sidewall region 1400.

The second shallow region 1102 is provided in two locations. One is provided between the first shallow regions 1101 and the other is provided in a region that is 180 degrees on the opposite side with the recessed regions 1211 sandwiched therebetween. Accordingly, one of the three finger tabs 324 is accommodated in a second shallow region 1102.

The second shallow regions 1102 are provided larger than the first shallow regions 1101 when viewed in plan. The second shallow regions 1102 are substantially the same depth as the first shallow regions 1101. Also, the second shallow regions 1102 are provided with an uneven nonslip region 1102t.

Next, the state where abdomen electrode pads 300 are accommodated in the pad tray 1000 will be described, with reference to FIG. 18. As shown in FIG. 18, in the present embodiment, an abdomen electrode pad 300 is accommodated in each of the eight recessed regions 1211, 1212, 1213, 1214, 1221, 1222, 1223 and 1224, such that the open ended side of the cylindrical body 322 of the abdomen electrode pad 300 is exposed.

The accommodated state of the abdomen electrode pad 300 in the recessed region 1211 will be described in detail, with reference to FIGS. 19 to 22. Note that since the accommodated state of the abdomen electrode pad 300 in the other recessed regions 1212, 1213, 1214, 1221, 1222, 1223 and 1224 is the same as the accommodated state of the abdomen electrode pad 300 in the recessed region 1211, redundant description will not be repeated.

Referring to FIGS. 19 and 20, an abutting portion 1110 is provided on a peripheral portion of the bottom region 1100 of the recessed region 1211. This abutting portion 1110 corresponds to a region where the edge (region shown by B2) of the base member 320 is exposed from the conductive gel 310 on the surface portion of the abdomen electrode pad 300 shown in FIG. 6, and is annularly provided along the sidewall region 1400.

In a state where the abdomen electrode pad 300 is accommodated in the recessed region 1211, the edge of the holding face 321 of the abdomen electrode pad 300 will be positioned on the abutting portion 1110. As a result, a predetermined gap (S) is formed between the holding face 321 of the abdomen electrode pad 300 and the bottom region 1100. This enables the conductive gel 310 to be poured onto the front side and the back side of the holding face 321.

Also, referring to FIGS. 19 and 21, an engaging region 322b that is provided thinner in thickness than the surrounding cylindrical body 322 is provided on the outer peripheral surface of the cylindrical body 322 in a region sandwiching a slit 322a with a finger tab 324, and a supporting region 1410 for engaging the engaging region 322b is provided on the sidewall region 1400.

In the present embodiment, the supporting region 1410 is a raised portion formed so as to project toward the inner periphery from the sidewall region 1400, with the supporting region 1410 being provided in a total of six locations in positions opposing the engaging regions 322b. When accommodating the abdomen electrode pad 300 in the recessed region 1211, the supporting regions 1410 are pushed by the outer wall of the cylindrical body 322 of the abdomen electrode pad 300 and elastically deform.

Thereafter, the elastic deformation is released by accommodation of the abdomen electrode pad 300 in the recessed region 1211 being completed, and the supporting regions 1410 engage the engaging regions 322b, with the supporting regions 1410 and the abutting portions 1110 sandwiching the electrode pad 300, and the electrode pad 300 being biased toward the bottom region 1100.

The state where the abdomen electrode pad 300 is accommodated in the recessed region 1211 can thereby be stabilized. Also, the base member 320 can be prevented from rising up when the conductive gel 310 is poured into the gap (S) between the holding face 321 of the abdomen electrode pad 300 and the bottom region 1100.

Mounting of Abdomen Electrode Pad 300 on Abdomen Electrode

Next, mounting of abdomen electrode pads 300 on abdomen electrodes will be described, with reference to FIGS. 22 to 27. Note that FIG. 22 is a plan view of a pad tray for accommodating abdomen electrode pads 300, and FIGS. 23 to 27 are first to fifth perspective views showing procedures for attaching abdomen electrode pads to abdomen electrodes using the pad tray for accommodating abdomen electrode pads.

Figure 22:
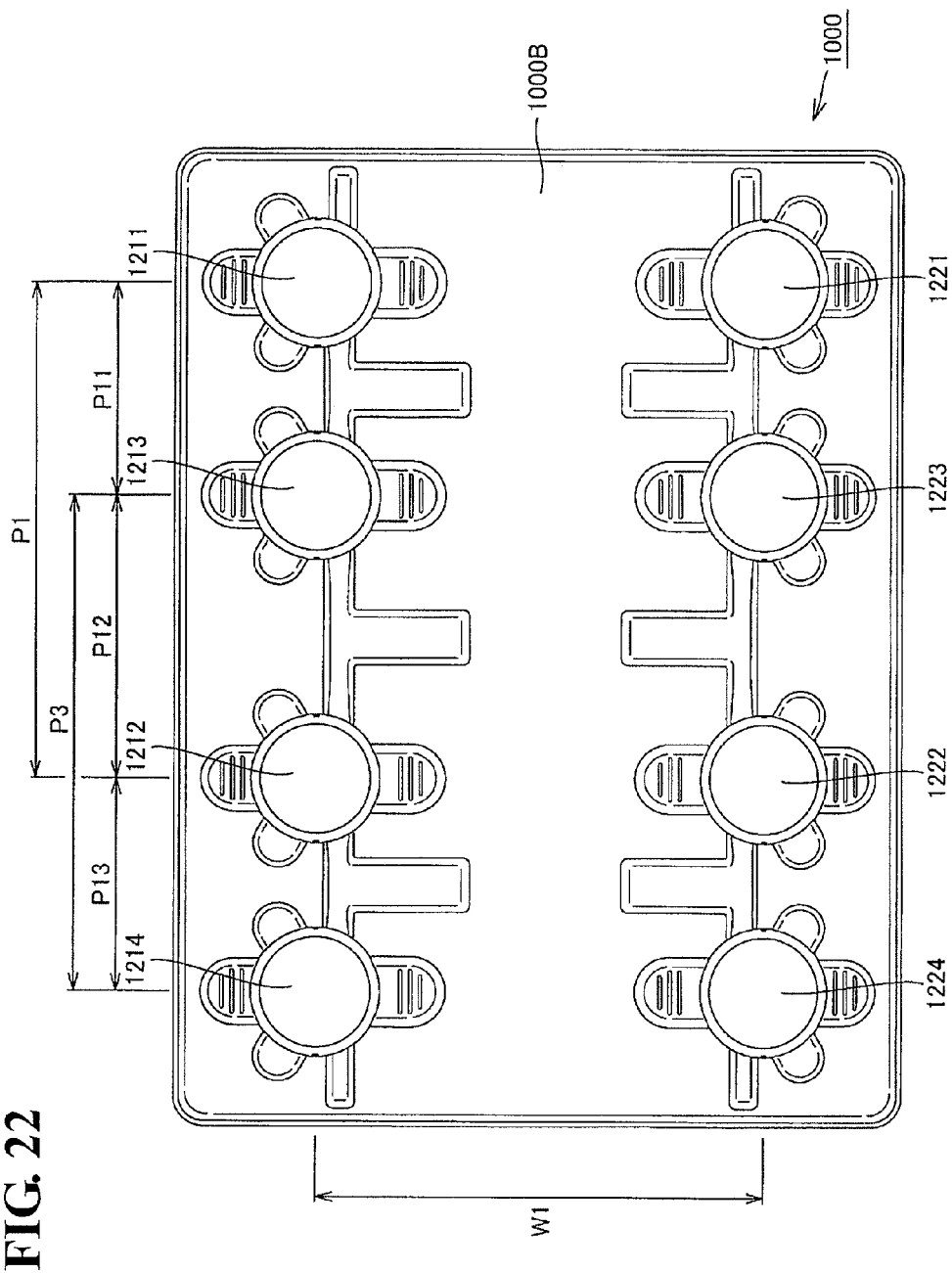
FIG. 22 is a plan view of the pad tray for accommodating abdomen electrode pads according to the embodiment.

Referring to FIG. 22, in the present embodiment, assuming that the accommodating region of the abdomen electrode pad 300 to be mounted on the abdomen electrode A11 is the first recessed region 1211, the accommodating region of the abdomen electrode pad 300 to be mounted on the abdomen electrode A12 is the second recessed region 1212, the accommodating region of the abdomen electrode pad 300 to be mounted on the abdomen electrode A13 is the third recessed region 1213, and the accommodating region of the abdomen electrode pad 300 to be mounted on the abdomen electrode A14 is the fourth recessed region 1214, the recessed regions 1211 to 1214 are arranged on the front side of the base portion 1000B in order of the first recessed region 1211, the third recessed region 1213, the second recessed region 1212 and the fourth recessed region 1214 in the direction of the long side 101b of the belt material 101.

Similarly, assuming that the accommodating region of the abdomen electrode pad 300 to be mounted on the abdomen electrode A21 is the first recessed region 1221, the accommodating region of the abdomen electrode pad 300 to be mounted on the abdomen electrode A22 is the second recessed region 1222, the accommodating region of the abdomen electrode pad 300 to be mounted on the abdomen electrode A23 is the third recessed region 1223, and the accommodating region of the abdomen electrode pad 300 to be mounted on the abdomen electrode A24 is the fourth recessed region 1224, the recessed regions 1221 to 1224 are arranged on the front side of the base portion 1000B in order of the first recessed region 1221, the third recessed region 1223, the second recessed region 1222 and the fourth recessed region 1224 in the direction of the long side 101b of the belt material 101.

The interval between the recessed regions 1211 to 1214 and the recessed regions 1221 to 1224 in the direction of the short side 101a is provided as W1, which is the same as the interval between the first to fourth electrodes A11 to A14 and the first to fourth electrodes A21 to A24 (see FIG. 4). Note that the dimension leader position of the recessed regions is the center position of the circular bottom regions 1100.

Also, the interval between the recessed region 1211 and the recessed region 1212 is provided as P11, the interval between the recessed region 1212 and the recessed region 1213 is provided as P12, and the interval between the recessed region 1213 and the recessed region 1214 is provided as P13 in the direction of the long side 101b of the belt material 101. Furthermore, the sum of P11 and P12 is provided so as to be the dimension P1 which is the interval between the abdomen electrode A11 and the abdomen electrode A12, and the sum of P12 and P13 is provided so as to be the dimension P3 which is the interval between the abdomen electrode A13 and the abdomen electrode A14 (see FIG. 4).

Similarly, the interval between the recessed region 1221 and the recessed region 1222 is provided as P11, the interval between the recessed region 1222 and the recessed region 1223 is provided as P12, and the interval between the recessed region 1223 and the recessed region 1224 is provided as P13, in the direction of the long side 101b of the belt material 101. Furthermore, the sum of P11 and P12 is provided so as to be the dimension P1 which is the interval between the abdomen electrode A21 and the abdomen electrode A22, and the sum of P12 and P13 is provided so as to be the dimension P3 which is the interval between the abdomen electrode A23 and the abdomen electrode A24 (see FIG. 4).

Procedures for Attachment of Abdomen Electrode Pad 300

Next, procedures for attaching abdomen electrode pads 300 to the abdomen electrodes A11 to A14 and A21 to A24 using the pad tray 1000 for accommodating abdomen electrode pads 300 will be described, with reference to FIGS. 23 to 27.

Figure 23:
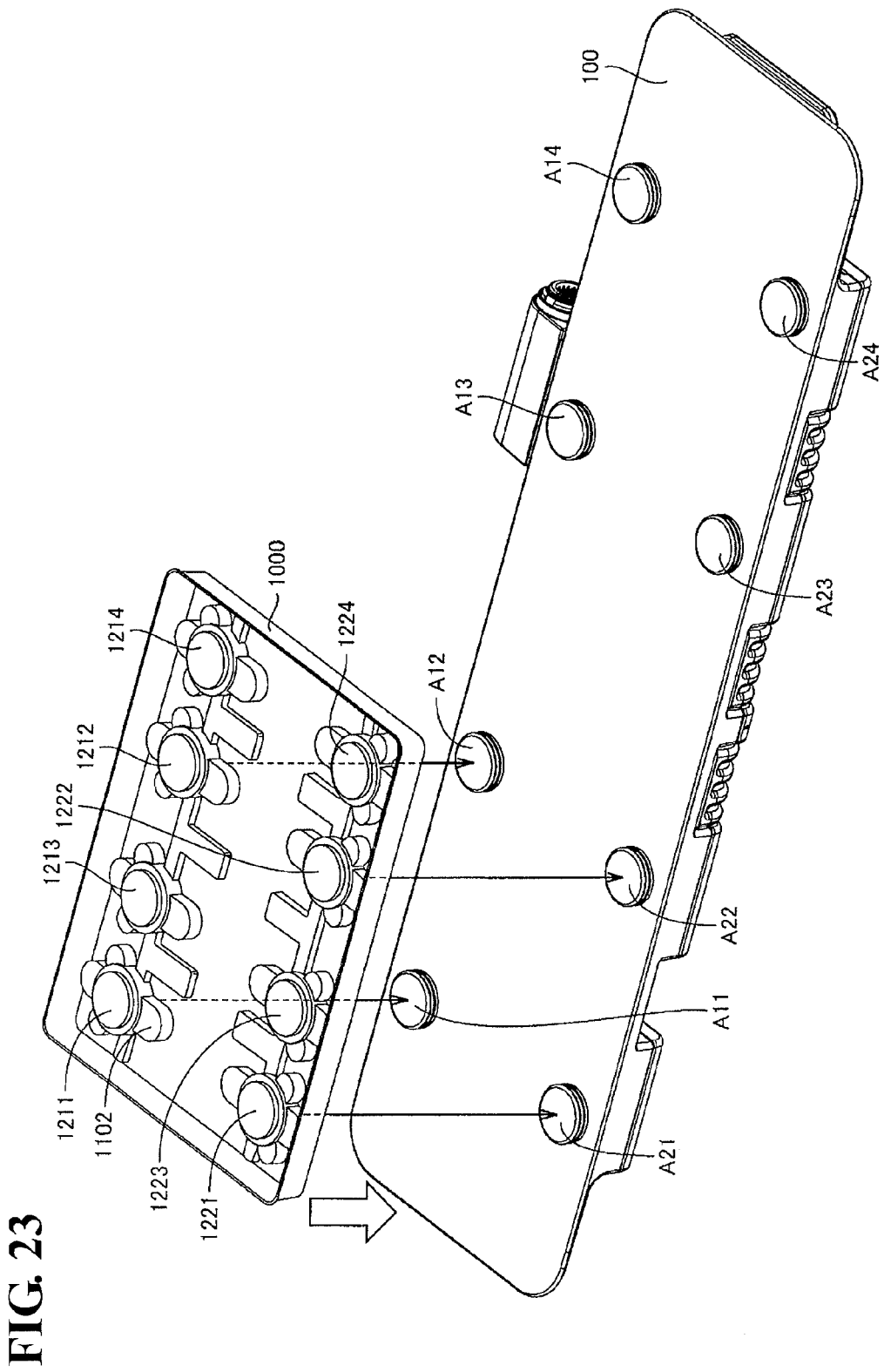
FIG. 23 is a first perspective view showing a procedure for attaching abdomen electrode pads to abdomen electrodes using the pad tray for accommodating abdomen electrode pads according to the embodiment.
Figure 24:
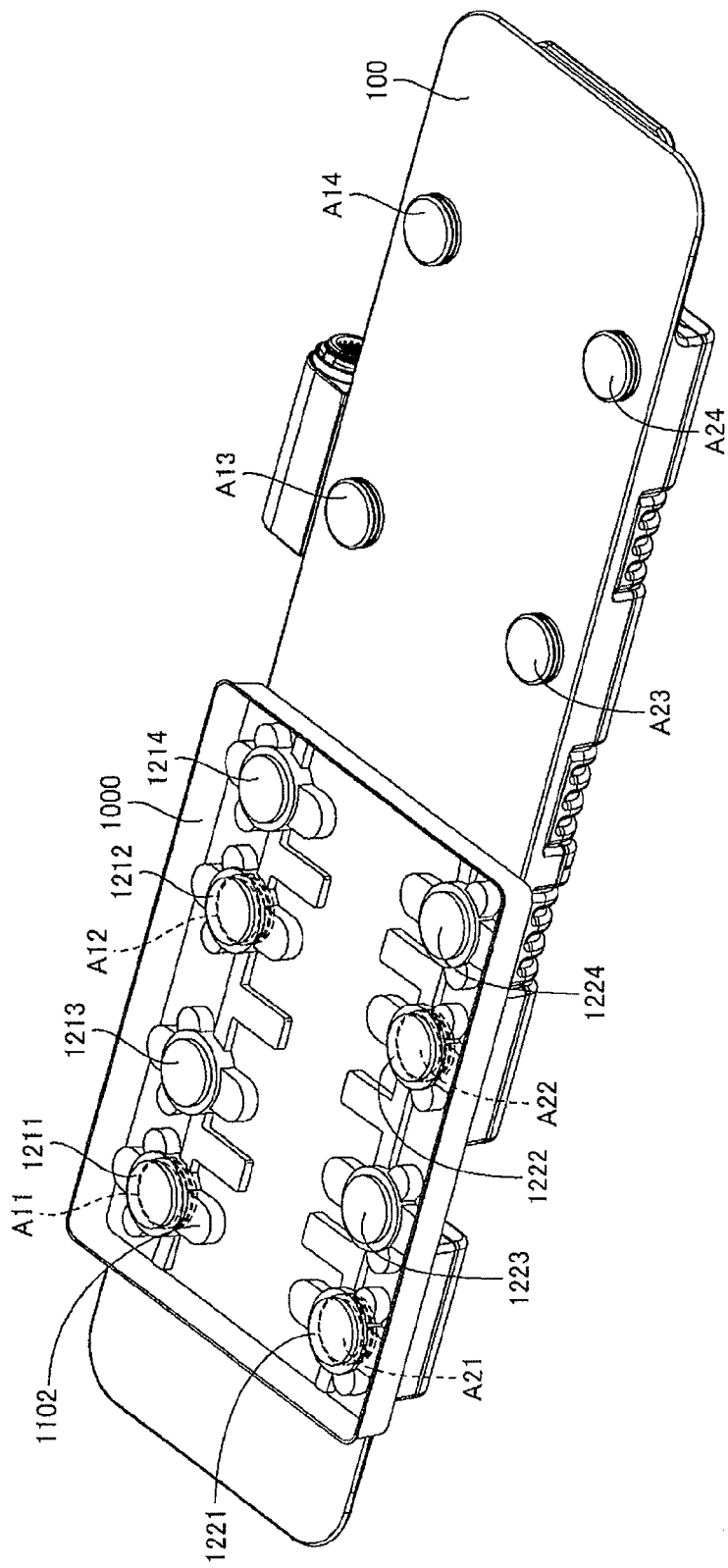
FIG. 24 is a second perspective view showing a procedure for attaching abdomen electrode pads to abdomen electrodes using the pad tray for accommodating abdomen electrode pads according to the embodiment.

First, as shown in FIG. 23, the recessed region 1211 is covered over the abdomen electrode A11, the recessed region 1212 is covered over the abdomen electrode A12, the recessed region 1221 is covered over the abdomen electrode A21 and the recessed region 1222 is covered over the abdomen electrode A22, in a state where the pad tray 1000 has been turned over. Thereafter, as shown in FIG. 24, the pad tray 1000 is pushed down toward the electrode belt 100. An electrode pad 300 is thereby mounted on each of the abdomen electrodes A11, A12, A21 and A22.

At this time, in the pad tray 1000 according to the present embodiment, the raised regions 323 that engage the outer peripheral surface of the abdomen electrodes A11 to A14 and A21 to A24 are provided in positions displaced from the engaging regions 322b and the supporting regions 1410 on the circumference.

When the pad tray 1000 is lifted up, the second shallow regions 1102 provided with the uneven nonslip regions 1102t are pushed down from the back side. The region around the supporting regions 1410 of the pad tray 1000 thereby deforms outward while the engaged state of the raised regions 323 with the abdomen electrode A22 is maintained, enabling the engagement relationship between the supporting regions 1410 of the pad tray 1000 and the engaging regions 322b of the abdomen electrode pads 300 to be easily released. Also, since there is no conductive gel 310 in the second shallow regions 1102, the conductive gel 310 does not collapse.

Note that the biasing force of the supporting regions 1410 that biases the abdomen electrode pad 300 toward the bottom region 1100 favorably is smaller than the force with which the raised regions 323 engage the outer peripheral surface of the abdomen electrodes A11 to A14 and A21 to A24.

The mounting of abdomen electrode pads 300 on the abdomen electrodes A11, A12, A21 and A22 is completed by the above procedures, as shown in FIG. 24.

Figure 25:
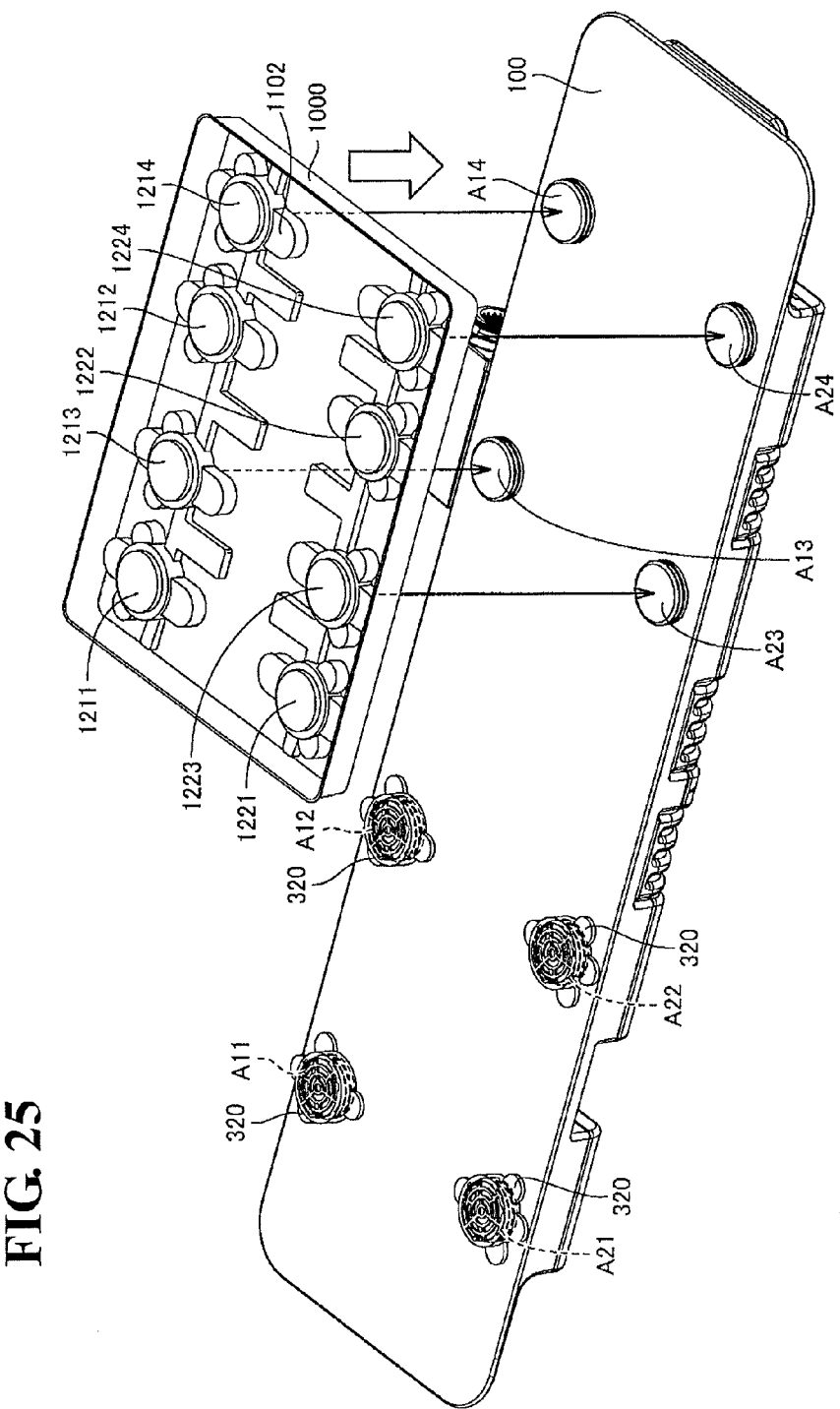
FIG. 25 is a third perspective view showing a procedure for attaching abdomen electrode pads to abdomen electrodes using the pad tray for accommodating abdomen electrode pads according to the embodiment.
Figure 26:
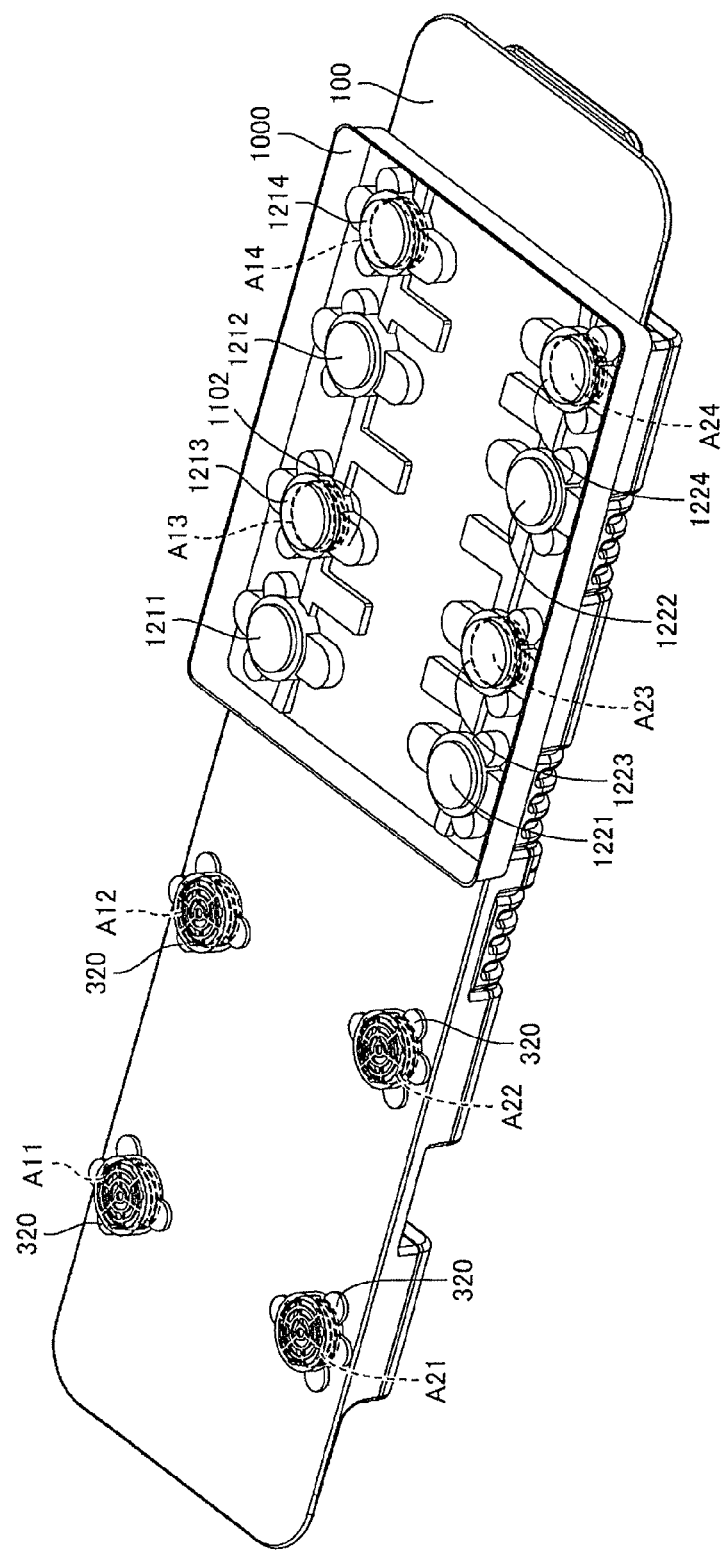
FIG. 26 is a fourth perspective view showing a procedure for attaching abdomen electrode pads to abdomen electrodes using the pad tray for accommodating abdomen electrode pads according to the embodiment.

Next, as shown in FIG. 25, similarly to the above, the recessed region 1213 is covered over the abdomen electrode A13, the recessed region 1214 is covered over the abdomen electrode A14, the recessed region 1223 is covered over the abdomen electrode A23 and the recessed region 1224 is covered over the abdomen electrode A24, in a state where the pad tray 1000 has been turned over. Thereafter, as shown in FIG. 26, the pad tray 1000 is pushed down toward the electrode belt 100. An abdomen electrode pad 300 is thereby mounted on each of the abdomen electrodes A13, A14, A23 and A24.

Figure 27:
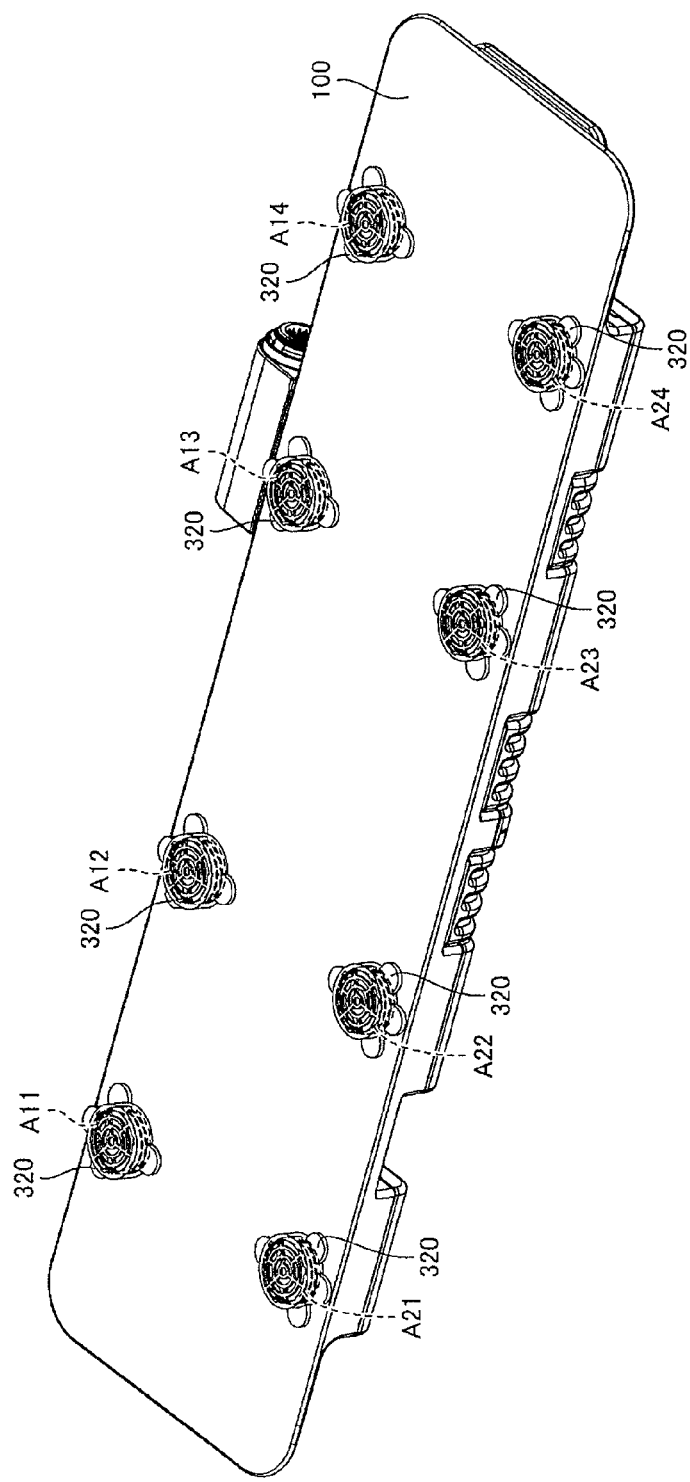
FIG. 27 is a fifth perspective view showing a procedure for attaching abdomen electrode pads to abdomen electrodes using the pad tray for accommodating abdomen electrode pads according to the embodiment.

Mounting of abdomen electrode pads 300 to the abdomen electrodes A11 to A14 and the abdomen electrodes A21 to A24 is completed by the above procedures, as shown in FIG. 27.

Note that it is also possible to prepare a pad tray having recessed regions arranged at the same intervals as the abdomen electrodes A11 to A14 and the abdomen electrodes A21 to A24, in which case the pad tray will be approximately the same size as the electrode belt 100.

On the other hand, with the pad tray 1000 according to the present embodiment, as shown in FIG. 22, the abdomen electrodes are divided into the two groups of the abdomen electrodes A11, 12, 21 and 22 (first group) and the abdomen electrodes A13, 14, 23 and 24 (second group), and the recessed regions are formed so that a recessed region of the second group is located between recessed regions of the first group. The pad tray 1000 can thereby be made smaller.

Note that all of the recessed regions for accommodating abdomen electrode pads 300 that are for mounting on abdomen electrodes need not necessarily be provided on a single pad tray, and the pad tray 1000 shown in FIG. 22 can also be configured so that a single pad tray is provided with only the recessed regions 1211, 1213, 1312 and 1214.

Figure 28:
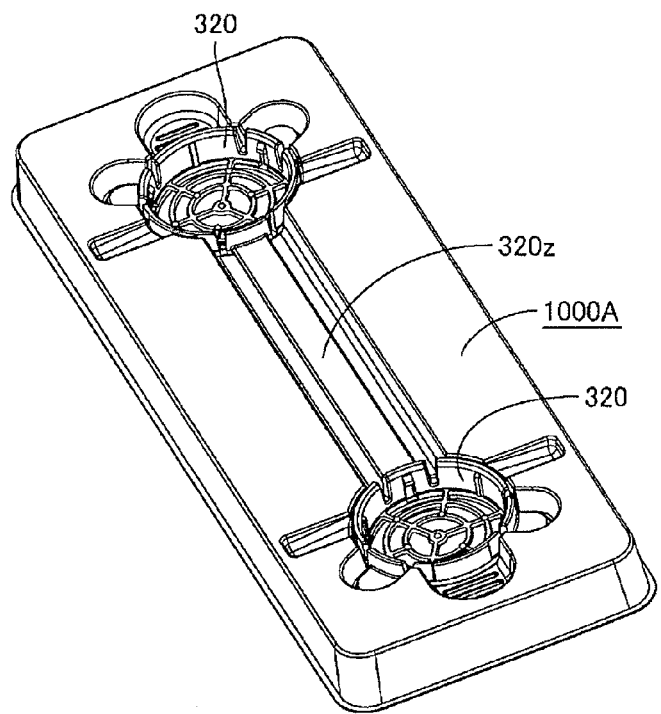
FIG. 28 is a perspective view of a pad tray of another configuration for accommodating abdomen electrode pads according to the embodiment.

Also, as shown with a pad tray 1000A shown in FIG. 28, a configuration providing two recessed regions in a single pad tray can also be adopted. Also, by providing a coupling member 320z that couples the two abdomen electrode pads 300, the two abdomen electrode pads 300 can be removed at the same time by lifting the coupling member 320z, when removing the abdomen electrode pads 320 from the abdomen electrodes.

As described above, handling of abdomen electrode pads 300 having a conductive gel is facilitated by using the above pad trays 1000 and 1000A, and mounting of abdomen electrode pads 300 on abdomen electrodes can be performed with ease.

Also, in the case where the abutting portion 1110 is provided on a peripheral portion of the bottom region 1100 of the recessed region 1211, the conductive gel 310 can be poured onto the front side and back side of the holding face 321, as a result of the predetermined gap (S) being formed between the holding face 321 of the abdomen electrode pad 300 and the bottom region 1100. By providing the supporting regions 1410, the base member 320 is prevented from rising up when the conductive gel 310 is poured in, and handling of the conductive gel 310 is facilitated.

Note that in the case of using abdomen electrode pads 300 to which the conductive gel 310 has been provided on the holding face 321 in advance, the abutting portion 1110 and the supporting regions 1410 need not necessarily be provided in the recessed region 1211.

Limb Clip 400 and Upper/Lower Limb Electrode 404

Next, the limb clip 400 will be described with reference to FIG. 29. Note that FIG. 29 is a diagram showing the structure of the limb clip 400.

Figure 29:
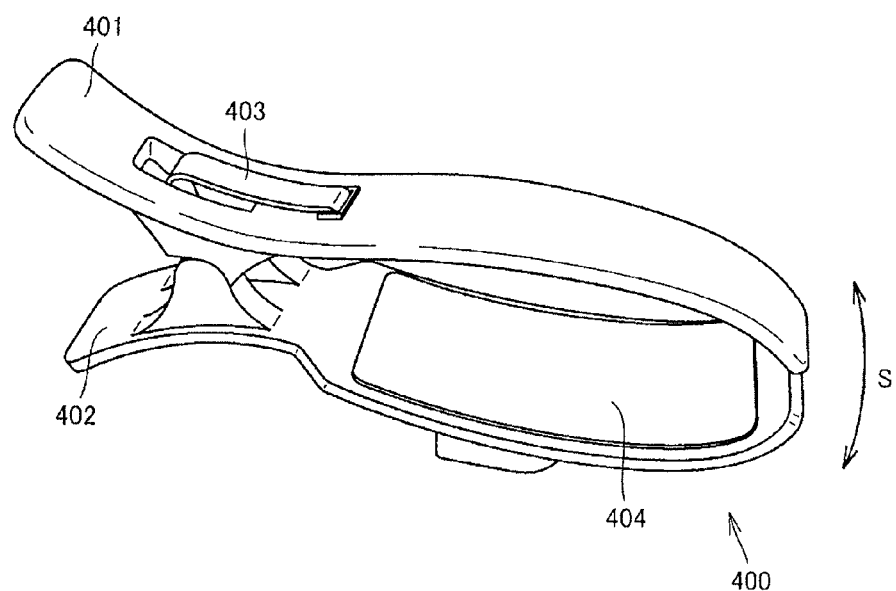
FIG. 29 is a diagram showing the structure of a limb clip for mounting an upper/lower-limb electrode according to the embodiment.

Referring to FIG. 29, the limb clip 400 has a first clamping clip 401 and a second clamping clip 402. The first clamping clip 401 and the second clamping clip 402 have gentle S-shapes that are symmetrical. The first clamping clip 401 and the second clamping clip 402 are coupled by an elastic clip 403 so as to be able to open and close in the direction of arrow S in the diagram.

A thin plate-like stainless steel upper/lower-limb electrode 404 that functions as the upper-limb electrodes H11 and H21 or the lower-limb electrodes F11 and F21 is attached to a curved portion of the second clamping clip 402 opposing the first clamping clip 401.

Upper/Lower Limb Electrode Pad 500

Next, an upper/lower-limb electrode pad 500 will be described, with reference to FIGS. 30 to 34. Note that FIG. 30 is a perspective view showing the structure of the upper/lower-limb electrode pad 500, FIG. 31 is a cross-sectional view along line XXXI-XXXI of FIG. 30, and FIG. 32 is a cross-sectional view along line XXXII-XXXII of FIG. 30.

Figure 30:
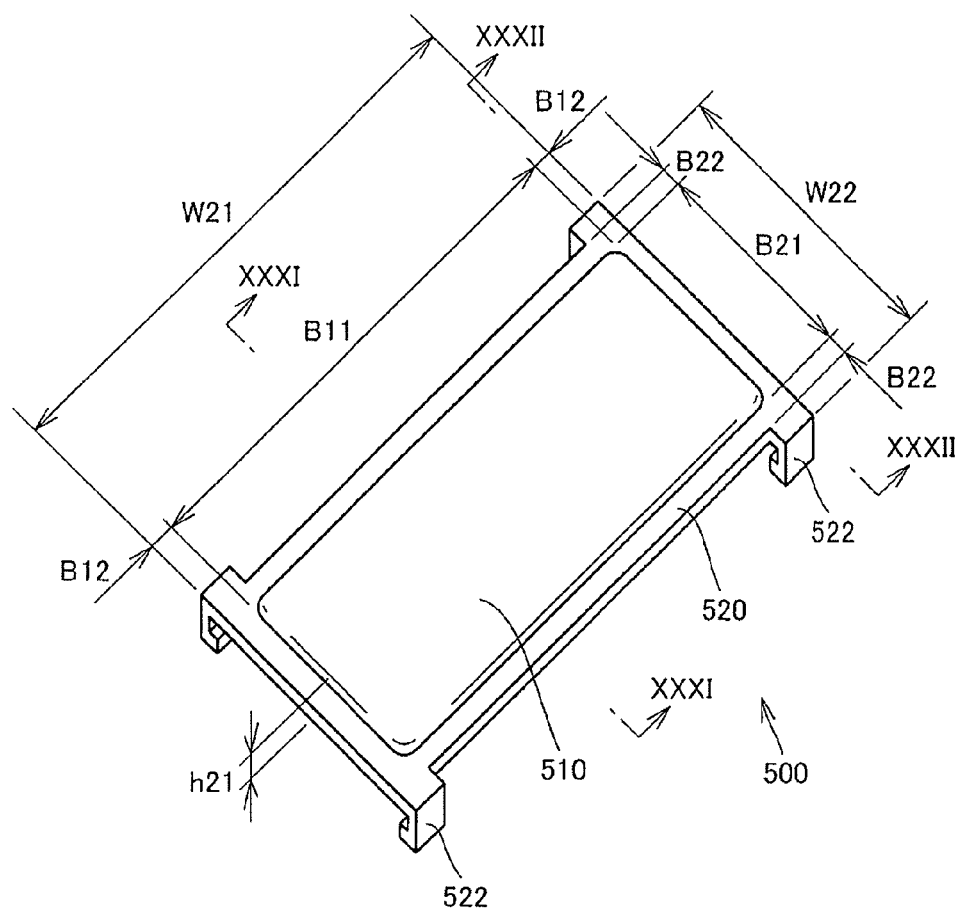
FIG. 30 is a perspective view showing the structure of an upper/lower-limb electrode pad according to the embodiment.
Figure 31:
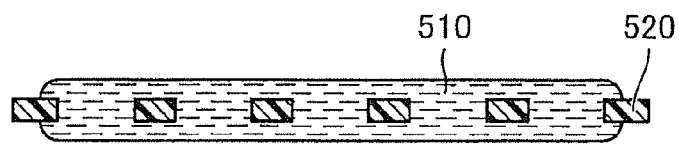
FIG. 31 is a cross-sectional view along line XXXI-XXXI of FIG. 30.
Figure 32:
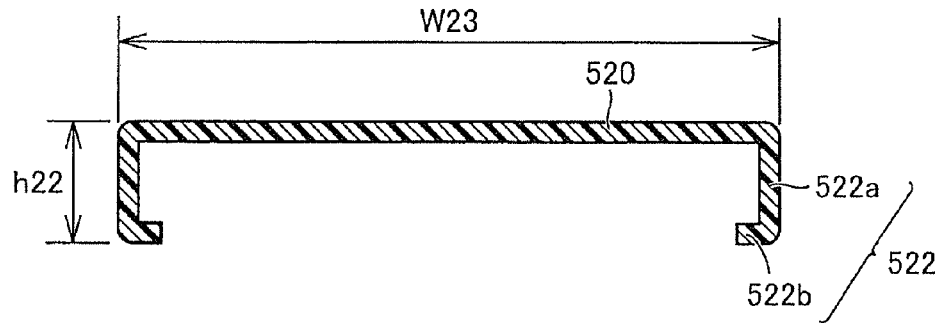
FIG. 32 is a cross-sectional view along line XXXII-XXXII of FIG. 30.

Referring to FIGS. 30 to 32, the upper/lower-limb electrode pad 500 is provided with an oblong rectangular conductive gel 510 and an approximately rectangular base member 520 that holds the conductive gel 510 so as to be electrically contactable with the upper/lower-limb electrode 404 and is provided so as to be attachable to and detachable from the upper/lower-limb electrode 404. Materials such as a polypropylene-based resin material or ABS resin are used for the base member 520. Gels such as an acrylic-based polymer gel or a urethane-based gel are used for the conductive gel 510.

The upper/lower-limb electrode pad 500 has a maximum length (W21) of approximately 77 mm, a maximum width (W22) of approximately 38 mm, and a height (h21) including the conductive gel 510 of approximately 9 mm. Also, on the surface portion of the upper/lower-limb electrode pad 500, the conductive gel 510 is held by the base member 520 so that the edge (region shown by B12 and B22) of the base member 520 is exposed.

In FIG. 30, the region on which the conductive gel 510 is provided (region shown by B11 and B21) has a dimension B11 of approximately 73 mm and a dimension B21 of approximately 30 mm, and the exposed edge (region shown by B12 and B22) has dimensions B12 and B22 both of approximately 2 mm. This enables the upper/lower-limb electrode pad 500 to be gripped without the fingertips coming in contact with the conductive gel 510.

An engaging region 522 is provided on each of the four corners of the base member 520. These engaging regions 522 each have an arm 522a that hangs down from the base member 520 and an engaging piece 522b that extends inward from the aim 522a in parallel to the base member 520. These engaging regions 522 can also be provided so as to be elastically deformable.

Attachment/Detachment of Upper/Lower Limb Electrode Pad 500 with Respect to Upper/Lower Limb Electrode 404

Next, the attachment and detachment of the upper/lower-limb electrode pad 500 with respect to the upper/lower-limb electrode 404 will be described, with reference to FIGS. 33 and 34. Note that FIG. 33 is a perspective view showing the attached state of the upper/lower-limb electrode pad to the upper/lower-limb electrode, and FIG. 34 is a cross-sectional view along line XXXIV-XXXIV of FIG. 33.

Figure 33:
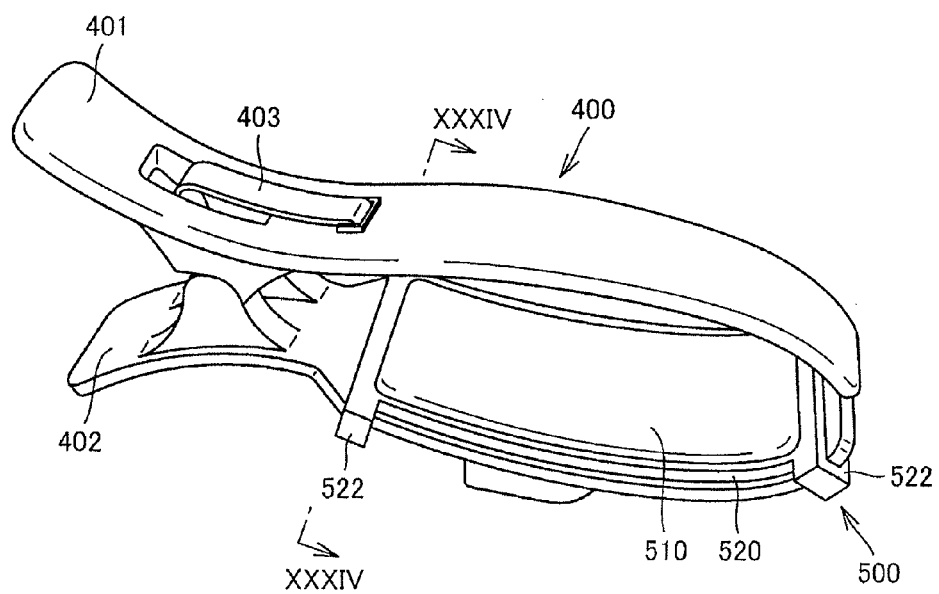
FIG. 33 is a perspective view showing a state where the upper/lower-limb electrode pad according to the embodiment is attached an upper/lower-limb electrode.
Figure 34:
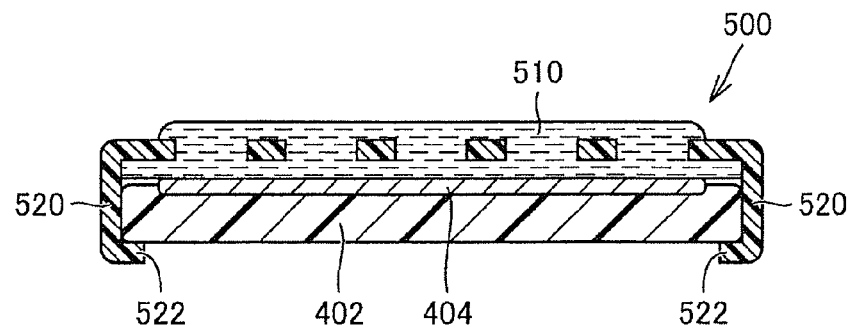
FIG. 34 is a cross-sectional view along line XXXIV-XXXIV of FIG. 33.

As shown in FIGS. 33 and 34, the upper/lower-limb electrode pad 500 is mounted on the upper/lower-limb electrode 404, by holding onto the upper/lower-limb electrode 404 and the second clamping clip 402, using the engaging regions 522 provided on the base member 520 of the upper/lower-limb electrode pad 500.

The bottom side of the conductive gel 510 provided on the upper/lower-limb electrode pad 500 thereby contacts the top portion of the upper/lower-limb electrode 404 in an electrically conductive manner. When removing the upper/lower-limb electrode pad 500 from the upper/lower-limb electrode 404, the base member 520 is held and pulled away with the fingers.

Detailed Structure of Base Member 520

Figure 35:
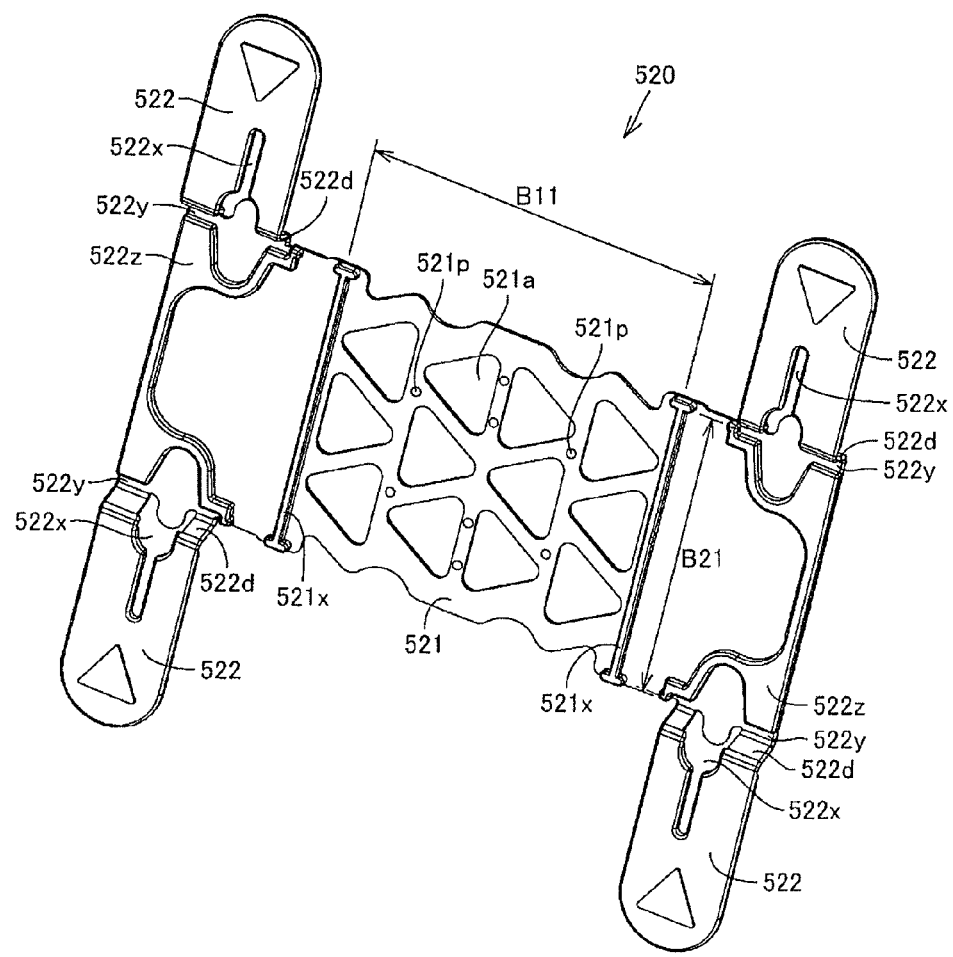
FIG. 35 is a perspective view showing the structure of a base member of the upper/lower-limb electrode pad according to the embodiment.

Next, the structure of the base member 520 will be described in detail, with reference to FIG. 35. Note that FIG. 35 is a perspective view showing the structure of the base member 520.

The base member 520 has an approximately rectangular shape overall, with a material such as a polypropylene-based resin material or ABS resin being used.

In a holding face 521 on which the conductive gel 510 is held, openings 521a having a triangular shape are arranged so that the oblique sides of triangles that are adjacently arranged in the vertical direction in the diagram are parallel to each other, thereby presenting a net-like configuration. Also, a plurality of protrusions 521p are provided on the holding face 521. Also, a pair of linear raised walls 521x are provided on the holding face 521, so as to define the region in which the conductive gel 510 is to be provided (region shown by B11 and B21 in FIG. 35).

The engaging regions 522 of the base member 520 are each coupled to the holding face 521 across an abutting portion 522d and a thin-walled portion 522y that constitutes a fragile region. An engaging hole 522x is provided in each of the engaging regions 522.

Also, in order to enhance the overall rigidity of the base member 520, thick-walled portions 522z that are thicker than the thickness of the holding face 521 in the region where the conductive gel 510 is to be provided are provided in the region of the holding face 521 to which the engaging regions 522 are coupled (region on the outer side of the region shown by B11 in FIG. 35).

Note that when attaching the base member 520 to the second clamping clip 402, engaging pins (not illustrated) provided on the side walls of the second clamping clip 402 are inserted into the engaging holes 522x.

Also, with this base member 520, the total area of the openings 521a in the region where the conductive gel 510 is provided (corresponds to region shown by B11 and B21 in FIG. 35) favorably is not less than 50% of the total area of the region where the conductive gel 510 is provided (corresponds to region shown by B11 and B21 in FIG. 35).

The release of air bubbles through the openings is thereby facilitated when applying the conductive gel 510 to the holding face 521, enabling the entrapment of air bubbles in the conductive gel 510 to be suppressed. As a result, flattening out of the conductive gel 510 over time in portions where there are air bubbles is prevented, and the measurement accuracy of the visceral fat measuring device can be stabilized.

Utilizing the openings 521a thus formed, the conductive gel 510 is applied to the front side and the back side of the holding face 521, and the conductive gel 510 is held on the holding face 521 so as to be integrally formed with the base member 520.

Detailed Structure of Pad Tray 2000

Figure 38:
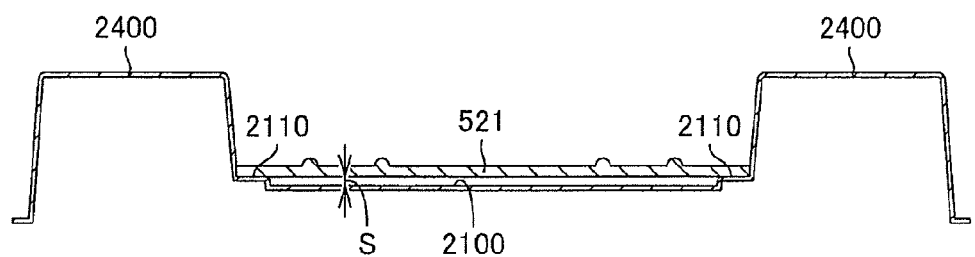
FIG. 38 is a cross-sectional view along line XXXVIII-XXXVIII of FIG. 37.
Figure 39:
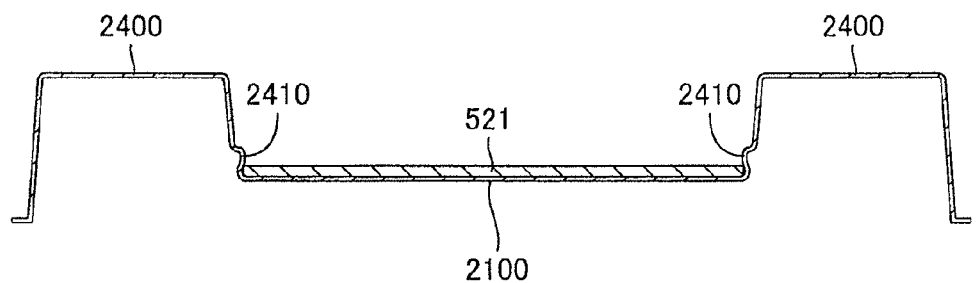
FIG. 39 is a cross-sectional view along line XXXIX-XXXIX of FIG. 37.

Next, the structure of a pad tray 2000 for accommodating upper/lower-limb electrode pads 500 having the above configuration will be described in detail, with reference to FIGS. 36 to 39. Note that FIG. 36 is a perspective view of a state where two upper/lower-limb electrode pads 500 are accommodated in the pad tray 2000, FIG. 37 is a perspective view of a state where one upper/lower-limb electrode pad 500 is accommodated in the pad tray 2000, FIG. 38 is a cross-sectional view along line XXXVIII-XXXVIII of FIG. 37, and FIG. 39 is a cross-sectional view along line XXXIX-XXXIX of FIG. 37.

Figure 36:
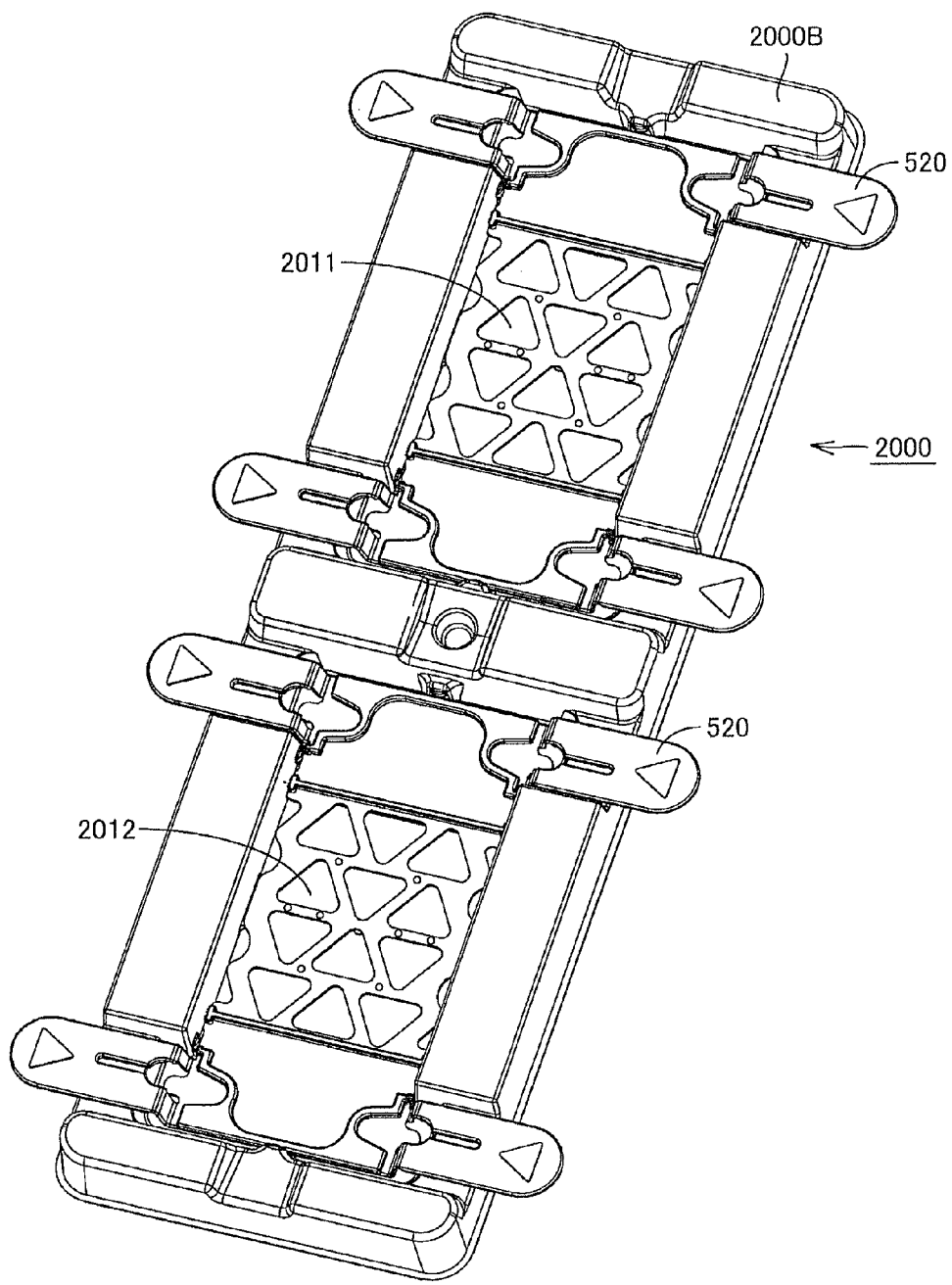
FIG. 36 is a perspective view of a state where two upper/lower-limb electrode pads are accommodated in a pad tray for accommodating upper/lower-limb electrode pads according to the embodiment.
Figure 37:
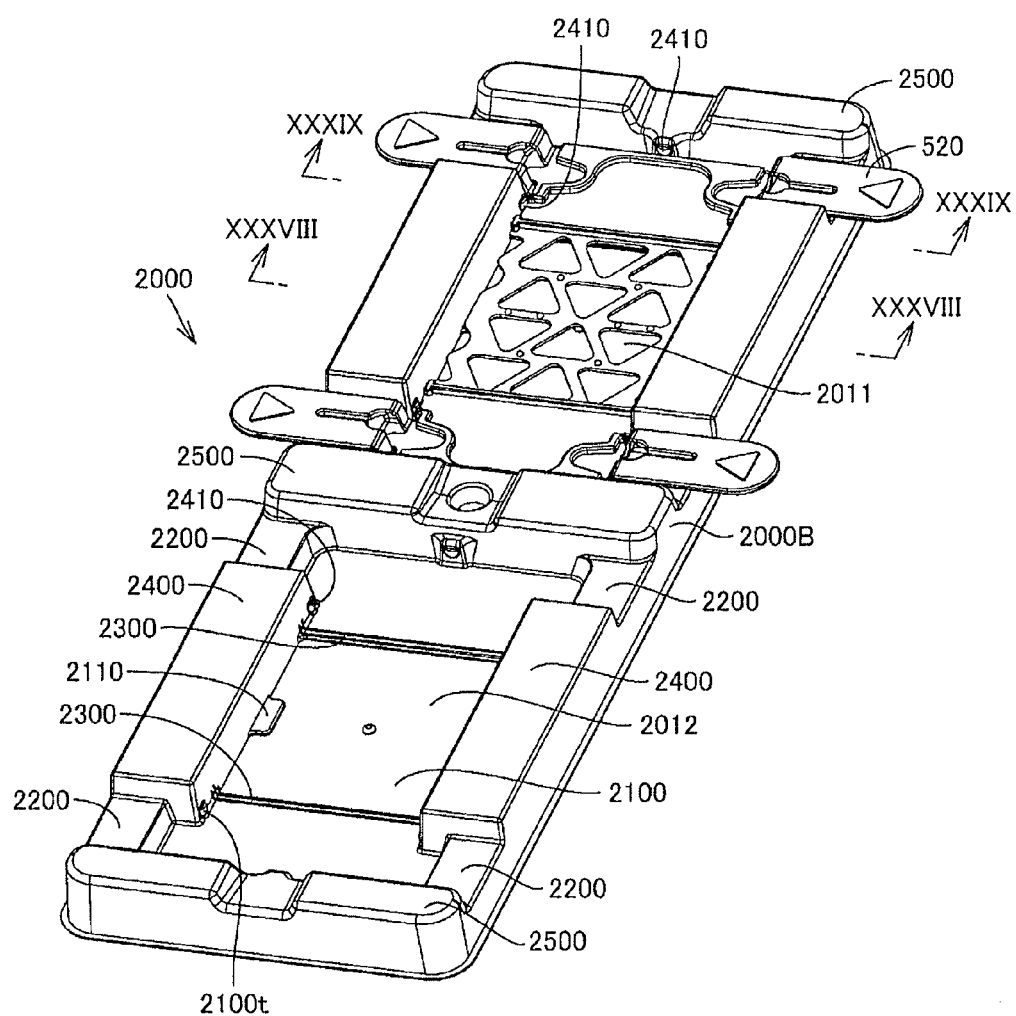
FIG. 37 is a perspective view of a state where one upper/lower-limb electrode pad is accommodated in the pad tray for accommodating upper/lower-limb electrode pads according to the embodiment.

Referring to FIG. 36 and FIG. 37, the pad tray 2000 according to the configuration of the present embodiment has a base portion 2000B having an approximately rectangular shape overall, and two recessed regions 2011 and 2012 that are formed in the front side of this base portion 2000B and are for accommodating upper/lower-limb electrode pads 500 having the abovementioned configuration. Note that the number of recessed regions is not limited to two, and is appropriately decided as needed.

In the present embodiment, a tabular resin molded article is used for the base portion 2000B. As for specific materials, a resin material selected from the group consisting of polyethylene terephthalate (PET), polyethylene (PE), polypropylene (PP), acrylonitrile butadiene styrene (ABS) and polystyrene (PS) is used. In the present embodiment, PET is used.

The shape of the recessed regions 2011 and 2012 will be described, with reference to FIGS. 36 and 37. In the present embodiment, the shape of the recessed region 2012 will be described, given that the recessed region 2011 and the recessed region 2012 have the same shape.

A recessed region 2012 has a rectangular bottom region 2100 and sidewall regions 2400 that extend up from the perimeter of this bottom region 2100 and surround the upper/lower-limb electrode pad 500 on both sides. Also, recessed wall regions 2200 that are lower in height than the sidewall regions 2400 and are for placing the engaging regions 522 provided on the upper/lower-limb electrode pad 500 are provided at the both ends of each sidewall region 2400.

Also, two gel retaining wall 2300 for defining the region in which the conductive gel 510 is to be poured are provided on the bottom region 2100 so as to couple the inner sides of the sidewall regions 2400 on both sides. In a state where the upper/lower-limb electrode pad 500 is placed in the recessed region 2012, the raised walls 521x are located over the gel retaining walls 2300.

A partition wall 2500 is provided between the recessed region 2011 and the recessed region 2012 and at the end of the recessed region 2012.

Referring to FIGS. 38 and 39, an abutting portion 2110 is provided on the bottom region 2100 in the approximate middle of each of the sidewall regions 2400 of the recessed region 2012. These abutting portions 2110 correspond to the region where the edge of the base member 520 (region shown by B22) will be exposed from the conductive gel 510, on the surface portion of the upper/lower-limb electrode pad 500 shown in FIG. 33.

As shown in FIG. 38, in a state where the upper/lower-limb electrode pad 500 is accommodated in the recessed region 2012, the edge of the base member 520 of the upper/lower-limb electrode pad 500 will be placed on the abutting portions 2110. As a result, a predetermined gap (S) will be formed between the holding face 521 of the upper/lower-limb electrode pad 500 and the bottom region 2100. The conductive gel 510 can thereby be poured onto the front side and the back side of the holding face 521.

Also, supporting regions 2410 are provided in positions that are a predetermined distance from the bottom region 2100, on the inner side of the sidewall regions 2400 that are on the outer side of the gel retaining walls 2300.

As shown in FIG. 39, in the present embodiment, the supporting regions 2410 are raised portions formed so as to project toward the inner periphery from the sidewall regions 1400, and are provided one at each end of the sidewall regions 2400, giving a total of four in one recessed region 2012.

The supporting regions 2410 are pushed by the ends of the holding face 521 and elastically deform when accommodating the upper/lower-limb electrode pad 500 in the recessed region 2012. Thereafter, the elastic deformation is released by accommodation of the upper/lower-limb electrode pad 500 in the recessed region 2012 being completed, with the supporting regions 2410 biasing the holding face 521 of the upper/lower-limb electrode pad 500 toward the bottom region 2100.

The state where the upper/lower-limb electrode pad 500 is accommodated in the recessed region 2012 can thereby be stabilized. The holding face 521 can also be prevented from rising up when the conductive gel 510 is poured into the gap (S) between the holding face 521 of the upper/lower-limb electrode pad 500 and the bottom region 2100.

Note that the present embodiment is not limited to the case where recessed regions 2011 and 2012 for accommodating two upper/lower-limb electrode pads 500 are provided in a single pad tray 2000. Configurations for accommodating one upper/lower-limb electrode pad 500 in a single pad tray or for accommodating three or more the upper/lower-limb electrode pads 500 in a single pad tray may be adopted.

As described above, handling of upper/lower-limb electrode pads 500 having a conductive gel is facilitated by using the above pad tray 2000.

Also, in the case where the abutting portions 2110 are provided on the edge of the bottom region 2100 of the recessed regions 2011 and 2012, the conductive gel 510 can be poured onto the front side and the back side of the holding face 521, as a result of the predetermined gap (S) being formed between the holding face 521 of the upper/lower-limb electrode pad 500 and the bottom region 2100. Also, by providing the supporting regions 2410, the base member 520 can be prevented from rising up when the conductive gel 510 is poured in, and handling of the conductive gel 510 is facilitated.

Note that in the case of using upper/lower-limb electrode pads 500 to which the conductive gel 510 has been provided on the holding face 521 in advance, the abutting portions 2110 and the supporting regions 2410 need not necessarily be provided in the recessed regions 2011 and 2012.

Note that although electrode pads for mounting electrodes to be used in a body fat measuring device and a pad tray for accommodating the electrode pads were described in the above embodiment, the electrode pads are not limited to electrodes for use in a body fat measuring device. For example, electrode pads and pad trays that are based on the present invention can be applied to electrodes for use in electrocardiograms, electromyograms, low frequency massagers, EMS (Electro Muscle Stimulation), electroencephalographs, and the like.

While embodiments of the present invention have been described above, the embodiments disclosed herein are to be considered in all respects as illustrative and not restrictive. The scope of the invention is defined by the claims, and all changes that come within the meaning and range of equivalency of the claims are intended to be embraced therein.

REFERENCE SIGNS LIST

1 Body fat measuring device
19 Control unit
11 Arithmetic processing unit
12 Impedance calculation unit
13 Various fat amount calculation unit
14 Body fat amount calculation unit
15 Site-specific fat amount calculation unit
16 Visceral fat amount calculation unit
17 Subcutaneous fat amount calculation unit
21 Constant current generation unit
22 Terminal changing unit
23 Potential difference detection unit
24 Physique information measurement unit
25 Subject information input unit
26 Display unit
27 Operation unit
28 Power supply unit
29 Memory unit
320, 520 Base member
100 Electrode belt
101 Belt material
101a Short side
101b Long side
200 Abdomen electrode
201 Cylindrical electrode portion
202 Recessed groove portion
300 Abdomen electrode pad
310, 510 Conductive gel
320z Coupling member
321, 521 Holding face
321a, 521a Opening
321p, 521p Protrusion
322 Cylindrical body
322a Slit
322b, 522 Engaging region
323 Raised region
324 Finger tab
400 Limb clip
401 First clamping clip
402 Second clamping clip
403 Elastic clip
404 Upper/lower-limb electrode
500 Upper/lower-limb electrode pad
521x Raised wall
522a Arm
522b Engaging piece
522d, 1110, 2110 Abutting portion
522x Engaging hole
522y Thin-walled portion
522z Thick-walled portion
1000, 1000A, 2000 Pad tray
1000B, 2000B Base portion
1100, 2100 Bottom region
1101 First shallow region
1102 Second shallow region
1211, 1221 Recessed region (first recessed region)
1212, 1222 Recessed region (second recessed region)
1213, 1223 Recessed region (third recessed region)
1214, 1224 Recessed region (fourth recessed region)
1400, 2400 Sidewall region
1410 Supporting region
2200 Recessed wall region
2300 Gel retaining wall
2500 Partition wall
AP1, AP2, AP3, AP4 Abdomen electrode pair
A11, A21 First electrode (abdomen electrode)
A12, A22 Second electrode (abdomen electrode)
A13, A23 Third electrode (abdomen electrode)
A14, A24 Fourth electrode (abdomen electrode)
F11, F21 Lower limb electrode
H11, H21 Upper limb electrode

The invention claimed is:

1. A pad tray system for accommodating an electrode pad that has a conductive gel and a holding face for holding the conductive gel so as to be contactable with an externally provided electrode and includes a base member that is provided so as to be attachable to and detachable from the electrode, the pad tray system comprising:
a base portion; and
a recessed region that is formed in a front side of the base portion and is for accommodating the electrode pad,
the recessed region having:
a bottom region; and
a sidewall region that extends up from the bottom region and is provided so as to surround the electrode pad, and
the recessed region further having:
a supporting region that projects inwardly toward a center of the pad tray from the sidewall region, and biases the electrode pad toward the bottom region in a state where the electrode pad is accommodated in the recessed region.

2. The pad tray system according to claim 1,
wherein the recessed region further includes an abutting portion that, when the electrode pad is accommodated, abuts the holding face and forms a predetermined gap between the holding face and the bottom region.

3. The pad tray system according to claim 1,
wherein the electrode has a cylindrical shape,
the electrode pad has a cylindrical shape open at one end, and has, on an inner side thereof, a raised region for engaging an outer peripheral surface of the electrode, and
the supporting region is provided in a position that is displaced from the raised region on a circumference when the electrode pad is accommodated in the recessed region.

4. The pad tray system according to claim 3,
wherein a force with which the electrode pad is sandwiched by the supporting region and the bottom region is smaller than a force with which the raised region engages the outer peripheral surface of the electrode.

5. The pad tray system according to claim 1, further comprising:
a belt material for holding the electrode,
wherein the electrode is arranged in a plurality of locations on the belt material at a predetermined interval, and
the recessed region is provided at an interval equal to the predetermined interval.

6. The pad tray system according to claim 5,
wherein the belt material has a rectangular shape having a short side and a long side,
the electrode is arranged, in a direction of the short side, in a plurality of locations on the belt material at a first short-side interval, and the recessed region is provided at an interval equal to the first short-side interval.

7. The pad tray system according to claim 5,
wherein the belt material has a rectangular shape having a short side and a long side,
the electrode is arranged, in a direction of the long side, at a plurality of locations on the belt material at a first long-side interval, and
the recessed region is provided at an interval equal to the first long-side interval.

8. The pad tray system according to claim 5,
wherein the belt material has a rectangular shape having a short side and a long side,
the electrode is arranged, in a direction of the short side, in a plurality of locations on the belt material at a first short-side interval,
the electrode is arranged, in a direction of the long side, at a plurality of locations on the belt material at a first long-side interval, and
the recessed region is provided at an interval equal to the first short-side interval in the direction of the short side, and at an interval equal to the first long-side interval in the direction of the long side.

9. The pad tray system according to claim 5,
wherein the belt material has a rectangular shape having a short side and a long side,
the electrode is arranged on the belt material in order of a first electrode, a second electrode, a third electrode and a fourth electrode in a direction of the long side,
the first electrode and the second electrode are arranged at a first long-side interval,
the second electrode and the third electrode are arranged at a second long-side interval,
the third electrode and the fourth electrode are arranged at a third long-side interval,
the recessed region has:
  a first recessed region for accommodating the first electrode;
  a second recessed region for accommodating the second electrode;
  a third recessed region for accommodating the third electrode; and
  a fourth recessed region for accommodating the fourth electrode,
  the first recessed region, the third recessed region, the second recessed region and the fourth recessed region are arranged in stated order on the front side of the base portion in the direction of the long side,
  an interval between the first recessed region and the second recessed region is provided at the first long-side interval, and
  an interval between the third recessed region and the fourth recessed region is provided at the third long-side interval.

10. The pad tray system according to claim 1,
wherein the pad tray is a tabular resin molded article.

11. The pad tray system according to claim 10,
wherein a resin material selected from the group consisting of polyethylene terephthalate, polyethylene, polypropylene, acrylonitrile butadiene styrene and polystyrene is used for the resin molded article.

12. The pad tray system according to claim 1,
wherein at least the recessed region of the pad tray is provided so as to enable the electrode pad to be visible from a back side, in a state where the electrode pad is accommodated in the recessed region.

13. The pad tray system according to claim 12,
wherein at least the recessed region of the pad tray has translucency.

\* \* \* \* \*